US007849489B2

(12) United States Patent
Bunn et al.

(10) Patent No.: US 7,849,489 B2
(45) **Date of Patent: *Dec. 7, 2010**

(54) SYSTEM AND METHOD FOR SUPPORTING EXTENDED PROTOCOLS IN A WIRELESS COMMUNICATION SYSTEM

(75) Inventors: Fred A. Bunn, Roswell, GA (US); Thomas L. Johnson, Gainesville, GA (US)

(73) Assignee: Broadcom Corporation, Irvine, CA (US)

(*) Notice: Subject to any disclaimer, the term of this patent is extended or adjusted under 35 U.S.C. 154(b) by 669 days.

This patent is subject to a terminal disclaimer.

(21) Appl. No.: 11/833,756

(22) Filed: Aug. 3, 2007

(65) Prior Publication Data

US 2007/0271588 A1 Nov. 22, 2007

Related U.S. Application Data

(63) Continuation of application No. 09/975,875, filed on Oct. 11, 2001, now Pat. No. 6,649,567.

(60) Provisional application No. 60/239,525, filed on Oct. 11, 2000, provisional application No. 60/239,526, filed on Oct. 11, 2000, provisional application No. 60/239,524, filed on Oct. 11, 2000, provisional application No. 60/239,530, filed on Oct. 11, 2000, provisional application No. 60/239,527, filed on Oct. 11, 2000, provisional application No. 60/240,550, filed on Oct. 13, 2000.

(51) Int. Cl.
*H04N 7/173* (2006.01)

(52) U.S. Cl. ....................... 725/111; 725/114; 725/116; 709/246; 370/477

(58) Field of Classification Search .................. 725/91, 725/111, 114, 116; 370/477; 709/246, 247
See application file for complete search history.

(56) References Cited

U.S. PATENT DOCUMENTS 5,293,379 A 3/1994 Carr (Continued)

FOREIGN PATENT DOCUMENTS

EP 0 806 852 A2 11/1997

(Continued)

OTHER PUBLICATIONS

Jacobson, V., "Compressing TCP/TP Headers for Low-Speed Serial Links", RFC 1144, Feb. 1990.

(Continued)

*Primary Examiner*—John W Miller
*Assistant Examiner*—Sumaiya A Chowdhury
(74) *Attorney, Agent, or Firm*—Sterne, Kessler, Goldstein & Fox P.L.L.C.

(57) ABSTRACT

A cable modem system and method is provided for supporting data transfer protocols that extend beyond standard protocols used in conventional data over cable systems. A cable modem in accordance with the invention determines, during registration, whether a CMTS with which it communicates is capable of supporting an extended protocol, and if it is, transfers data to the CMTS in accordance with the extended protocol. Additionally, a CMTS in accordance with the invention is notified during registration whether or not a cable modem supports an extended protocol and stores this information. When a request for transmission opportunity is subsequently received from the cable modem, the CMTS accesses the stored information to determine if the cable modem supports the extended protocol. If the cable modem supports the extended protocol, the CMTS processes data received from the cable modem during the transmission opportunity in accordance with that protocol.

20 Claims, 30 Drawing Sheets

U.S. PATENT DOCUMENTS 5,307,413 A 4/1994 Denzer
5,530,645 A 6/1996 Chu
5,646,617 A 7/1997 Ohmoto et al.
5,737,733 A 4/1998 Eller
5,831,558 A 11/1998 Harvell
5,987,022 A * 11/1999 Geiger et al. ............... 370/349
6,032,197 A 2/2000 Birdwell et al.
6,078,955 A 6/2000 Konno et al.
6,181,716 B1 1/2001 Lide
6,195,391 B1 2/2001 Hancock et al.
6,198,735 B1 3/2001 Pazhyannur et al.
6,295,481 B1 9/2001 Price
6,300,887 B1 10/2001 Le
6,434,168 B1 8/2002 Kari
6,438,123 B1 * 8/2002 Chapman .................... 370/351
6,529,912 B2 3/2003 Satoh et al.
6,535,925 B1 3/2003 Svambro et al.
6,542,504 B1 4/2003 Mahler et al.
6,542,931 B1 4/2003 Le et al.
6,594,280 B1 7/2003 Chapman
6,765,925 B1 7/2004 Sawyer et al.
6,788,707 B1 9/2004 Horton, Jr. et al.
6,882,637 B1 4/2005 Le et al.
6,889,385 B1 5/2005 Rakib et al.
6,901,049 B1 5/2005 Chapman
6,909,715 B1 6/2005 Denney et al.
6,963,931 B2 11/2005 Bunn et al.
6,986,157 B1 1/2006 Fijolek et al.
7,130,314 B2 10/2006 Bunn et al.
7,275,115 B2 9/2007 Bunn et al.
2001/0004768 A1 6/2001 Hodge et al.
2002/0029206 A1 3/2002 Satoh et al.
2002/0049861 A1 4/2002 Bunn et al.
2002/0062394 A1 5/2002 Bunn et al.
2002/0073227 A1 6/2002 Bunn et al.
2002/0080868 A1 6/2002 Bunn et al.
2002/0106029 A1 8/2002 Bunn et al.
2002/0191691 A1 12/2002 Holborow
2003/0185245 A1 10/2003 Kang et al.
2005/0030944 A1 2/2005 Lazarus et al.

FOREIGN PATENT DOCUMENTS

EP 0 933 876 A1 8/1999

OTHER PUBLICATIONS

International Preliminary Examination Report for PCT/US01/31559, dated Nov. 25, 2002,(4 pages).

"Transparent Automoding Procedure between a Local (Client) Modem and a Remote (Server) Modem," *Research Disclosure,* Kenneth Mason Publications, Aug. 1999, pp. 1138-1139.

Perkins, S.J. and Mutka, M.W., "Dependency Removal for Transport Protocol Header Compression over Noisy Channels," *IEEE,* 1997, pp. 1025-1029.

Salomon, D., Data Compression: The Complete Reference, Springer, US, New York, NY, 1998, pp. 101-162 and 357-360.

Casner, S. et al., "Compressing IP/UDP/RTP Headers for Low-Speed Serial Links," Network Working Group, Feb. 1999, pp. 1-23.

"Radio Frequency Interface Specification SP-RFIv1.1-I05-000714," Data-Over-Cable Service Interface Specifications, Jul. 14, 2000, retrieved from the Internet on May 20, 2002:<URL:http://www.docsis.org/docs/SP-RFIv1.1-I05-000714.pdf>, pp. i-xviii, 1-6, 15-21, 93-100, 143-178.

Jacobson, V., "Compressing TCP/IP Headers," RFC 1144, *Network Working Group,* Feb. 1990, pp. 1-43.

International Search Report issued Apr. 4, 2002 for Appln. No. PCT/US01/31556, 7 pages.

International Search Report issued Apr. 4, 2002 for Appln. No. PCT/US01/31553, 7 pages.

International Search Report issued Apr. 12, 2002 for Appln. No. PCT/US01/31554, 7 Pages.

International Search Report issued Apr. 12, 2002 for Appln. No. PCT/US01/31559, 6 pages.

International Search Report issued Apr. 12, 2002 for Appln. No. PCT/US01/31567, 6 pages.

* cited by examiner

SYSTEM AND METHOD FOR SUPPORTING EXTENDED PROTOCOLS IN A WIRELESS COMMUNICATION SYSTEM

CROSS-REFERENCE TO RELATED APPLICATIONS

This application is a continuation of U.S. Non-Provisional application Ser. No. 09/973,875, filed Oct. 11, 2001, which claims benefit to U.S. Provisional Patent Application No. 60/239,525, filed Oct. 11, 2000, U.S. Provisional Patent Application No. 60/239,526, filed Oct. 11, 2000, U.S. Provisional Patent Application No. 60/239,524, filed Oct. 11, 2000, U.S. Provisional Patent Application No. 60/239,530, filed Oct. 11, 2000, U.S. Provisional Patent Application No. 60/239,527, filed Oct. 11, 2000, U.S. Provisional Patent Application No. 60/240,550, filed Oct. 13, 2000, all of which are incorporated by reference in its entirety herein.

This application is related to the following non-provisional applications:

"Cable Modem System and Method for Dynamically Mixing Protocol Specific Header Suppression Techniques," U.S. Non-Provisional application Ser. No. 09/973,781, filed Oct. 11, 2001, now U.S. Pat. No. 6,963,931, Issued Nov. 8, 2005, and incorporated by reference herein in its entirety.

"Efficiently Transmitting RTP Protocol in a Network that Guarantees In Order Delivery of Packets," U.S. Non-Provisional application Ser. No. 09/973,872, filed Oct. 11, 2001, now U.S. Pat. No. 7,130,314, Issued Oct. 31, 2006, and incorporated by reference herein in its entirety.

"Dynamic Delta Encoding for Cable Modem Header Suppression," U.S. Non-Provisional application Ser. No. 09/973,871, filed Oct. 11, 2001, now pending and incorporated by reference herein in its entirety.

"Cable Modem System and Method for Supporting Packet PDU Data Compression," U.S. Non-Provisional application Ser. No. 09/973,783, filed Oct. 11, 2001, now allowed and incorporated by reference herein in its entirety.

BACKGROUND OF THE INVENTION

1. Field of the Invention

The present invention is generally related to communication systems. More particularly, the present invention is related to cable modem systems and methods for transferring data.

2. Background Art

In conventional cable modem systems, a hybrid fiber-coaxial (HFC) network provides a point-to-multipoint topology for supporting data communication between a cable modem termination system (CMTS) at the cable headend and multiple cable modems (CM) at the customer premises. In such systems, information is broadcast downstream from the CMTS to the cable modems as a continuous transmitted signal in accordance with a time division multiplexing (TDM) technique. In contrast, information is transmitted upstream from each of the cable modems to the CMTS as short burst signals in accordance with a time domain multiple access (TDMA) technique. The upstream transmission of data from the cable modems is managed by the CMTS, which allots to each cable modem specific slots of time within which to transfer data.

Conventional cable modem systems are asymmetrical in that there is considerably less bandwidth available for upstream transmissions than there is for downstream transmissions. This lack of upstream bandwidth is further exacerbated by the fact that the upstream channels must be shared by multiple cable modems. As a result, the conservation of upstream bandwidth is imperative in order to maintain overall system performance. This is particularly true where cable modem users are engaging in activities that require both substantial upstream and downstream bandwidth, such as IP telephony, video teleconferencing and Internet gaming.

Conventional cable modem systems utilize DOCSIS-compliant equipment and protocols to carry out the transfer of data packets between multiple cable modems and a CMTS. The term DOCSIS (Data Over Cable System Interface Specification) generally refers to a group of specifications published by CableLabs that define industry standards for cable headend and cable modem equipment. In part, DOCSIS sets forth requirements and objectives for various aspects of cable modem systems including operations support systems, management, data interfaces, as well as network layer, data link layer, and physical layer transport for data over cable systems. The most current version of the DOCSIS specification is DOCSIS 1.1.

It has been observed, however, that the use of proprietary data transfer protocols that extend beyond those provided by the DOCSIS specification may be advantageous in conserving network bandwidth in a cable modem system. This is particularly true with respect to Payload Header Suppression (PHS). PHS, as defined by DOCSIS 1.1, allows for the suppression of unnecessary Ethernet/IP header information in the payload of a DOCSIS packet by the cable modem and subsequent reconstruction of the header by the CMTS. The goal of PHS is to reduce the number of bits transferred per packet, thereby improving network bandwidth utilization. However, DOCSIS PHS (DPHS) only permits header suppression based on the presence of redundant header bytes in sequentially-transmitted packets. It would be desirable to utilize more efficient payload header suppression techniques in transferring data over a cable modem network. In particular, it would be desirable to utilize proprietary protocol-specific header suppression techniques that permit greater reduction in the size of the payload headers within a given DOCSIS packet than that provided by DOCSIS 1.1.

The use of proprietary data transfer protocols that extend beyond DOCSIS may be desirable for a number of additional reasons. For example, the DOCSIS specification does not provide a mechanism for identifying TCP/IP or RTP data streams within a cable modem service flow. As a result, DOCSIS does not allow for the specialized handling of such TCP/IP or RTP data streams in a manner that provides for better utilization of network bandwidth (e.g., protocol-specific suppression of non-header information). Furthermore, although DOCSIS 1.1 provides techniques for the fragmentation of very large packets into multiple upstream bursts and the concatenation of multiple small packets into a single upstream burst, more efficient packet fragmentation and concatenation techniques may be achieved.

Heretofore, the use of proprietary data transfer protocols that extend beyond those provided by the DOCSIS specification have been avoided. This is due, in part, to the fact that the DOCSIS specification does not provide a mechanism for using alternative protocols in a cable modem system. For example, the DOCSIS specification does not provide a mechanism for the use of data packet formats other than those it provides. Moreover, because conventional CMTS and cable modem devices have been designed in accordance with the DOCSIS specification, the use of extended protocols have been avoided to ensure interoperability between individual cable modem system components. For example, conventional DOCSIS-compliant CMTS equipment is incapable of differentiating between standard DOCSIS traffic and traffic transmitted in accordance with an extended protocol.

Accordingly, what is desired is a system and method for transferring data in a cable modem network that supports the use of protocols that extend beyond the DOCSIS specification. For example, the desired system and method should support the use of protocol-specific packet header suppression techniques that are more efficient than DPHS. However, the desired system and method should be interoperable with DOCSIS in the sense that components of a cable modem system that support the extended protocols can exist on the same network with components that do not. Furthermore, the desired system and method should require very little modification to existing cable modem system components, such as existing cable modem and CMTS equipment.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the pertinent art to make and use the invention.

Figure 1:
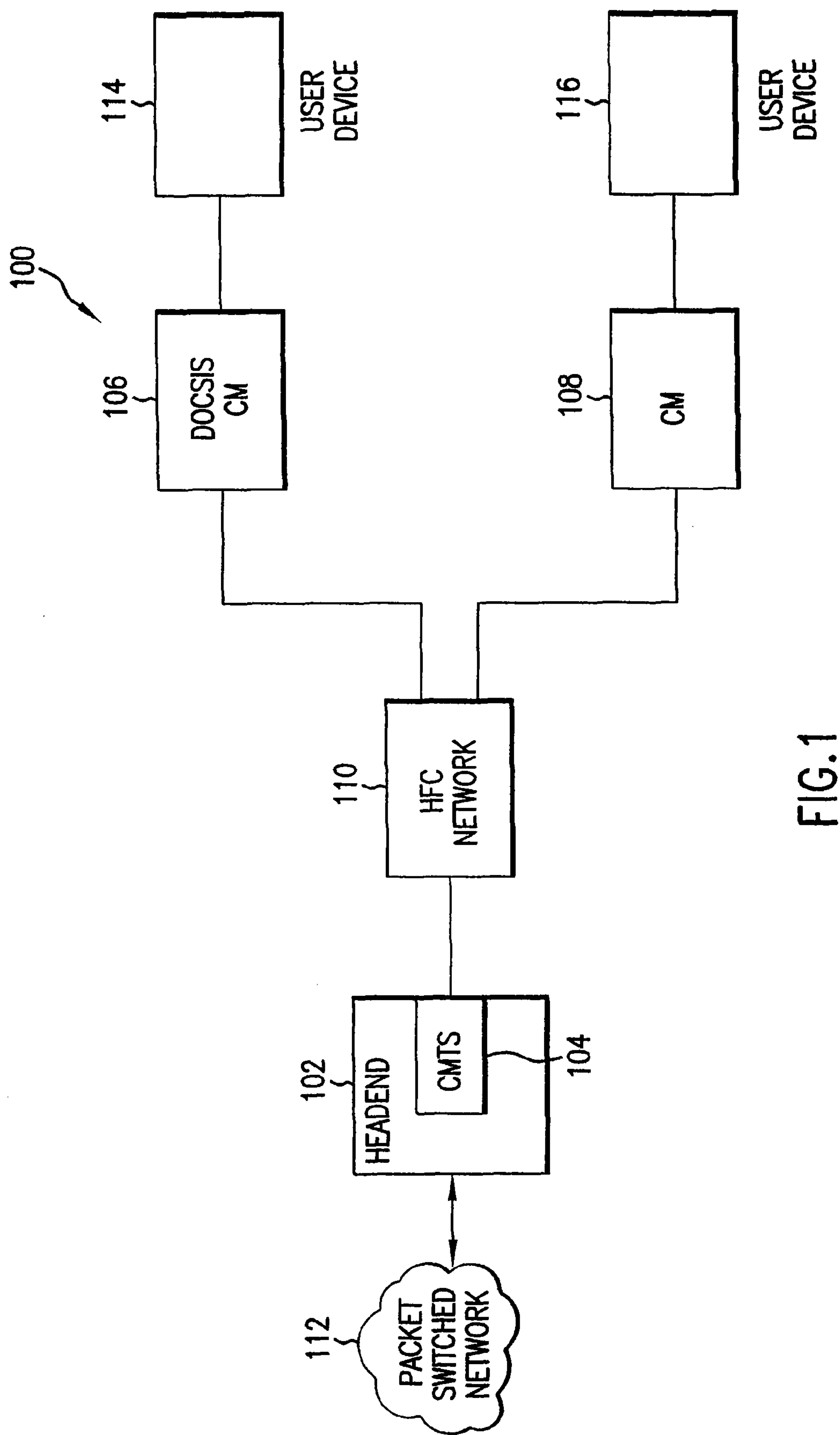
FIG. 1 is a high level block diagram of a cable modem system in accordance with embodiments of the present invention.

The features, objects, and advantages of the present invention will become more apparent from the detailed description set forth below when taken in conjunction with the drawings in which like reference characters identify corresponding elements throughout. In the drawings, like reference numbers generally indicate identical, functionally similar, and/or structurally similar elements. The drawings in which an element first appears is indicated by the leftmost digit(s) in the corresponding reference number.

DETAILED DESCRIPTION OF THE INVENTION

Table of Contents

A. Cable Modem System in Accordance with Embodiments of the Present Invention
B. Example Cable Modem System Components in Accordance with Embodiments of the Present Invention
C. Supporting Extended Data Transfer Protocols in Accordance with Embodiments of the Present Invention
  1. Packet Header Suppression
  2. Packet Header Expansion
  3. RTP Header Suppression
  4. Dynamic Delta Encoding Scheme
D. Environment
E. Conclusion While the present invention is described herein with reference to illustrative embodiments for particular applications, it should be understood that the invention is not limited thereto. Those skilled in the art with access to the teachings provided herein will recognize additional modifications, applications, and embodiments within the scope thereof and additional fields in which the present invention would be of significant utility.

A. Cable Modem System in Accordance with Embodiments of the Present Invention

FIG. 1 is a high level block diagram of an example cable modem system 100 in accordance with embodiments of the present invention. The cable modem system 100 enables voice communications, video and data services based on a bi-directional transfer of packet-based traffic, such as Internet protocol (IP) traffic, between a cable system headend 102 and a plurality of cable modems over a hybrid fiber-coaxial (HFC) cable network 110. In the example cable modem system 100, only two cable modems 106 and 108 are shown for clarity. In general, any number of cable modems may be included in the cable modem system of the present invention.

The cable headend 102 is comprised of at least one cable modem termination system (CMTS) 104. The CMTS 104 is the portion of the cable headend 102 that manages the upstream and downstream transfer of data between the cable headend 102 and the cable modems 106 and 108, which are located at the customer premises. The CMTS 104 broadcasts information downstream to the cable modems 106 and 108 as a continuous transmitted signal in accordance with a time division multiplexing (TDM) technique. Additionally, the CMTS 104 controls the upstream transmission of data from the cable modems 106 and 108 to itself by assigning to each cable modem 106 and 108 short grants of time within which to transfer data. In accordance with this time domain multiple access (TDMA) technique, each cable modem 106 and 108 may only send information upstream as short burst signals during a transmission opportunity allocated to it by the CMTS 104.

As shown in FIG. 1, the CMTS 102 further serves as an interface between the HFC network 110 and a packet-switched network 112, transferring IP packets received from the cable modems 106 and 108 to the packet-switched network 112 and transferring IP packets received from the packet-switched network 112 to the cable modems 106 and 108 when appropriate. In embodiments, the packet-switched network 112 comprises the Internet.

In addition to the CMTS 104, the cable headend 102 may also include one or more Internet routers to facilitate the connection between the CMTS 104 and the packet-switched network 112, as well as one or more servers for performing necessary network management tasks.

The HFC network 110 provides a point-to-multipoint topology for the high-speed, reliable, and secure transport of data between the cable headend 102 and the cable modems 106 and 108 at the customer premises. As will be appreciated by persons skilled in the relevant art(s), the HFC network 110 may comprise coaxial cable, fiberoptic cable, or a combination of coaxial cable and fiberoptic cable linked via one or more fiber nodes.

Each of the cable modems 106 and 108 operates as an interface between the HFC network 110 and at least one attached user device. In particular, the cable modems 106 and 108 perform the functions necessary to convert downstream signals received over the HFC network 110 into IP data packets for receipt by an attached user device. Additionally, the cable modems 106 and 108 perform the functions necessary to convert IP data packets received from the attached user device into upstream burst signals suitable for transfer over the HFC network 110. In the example cable modem system 100, each cable modem 106 and 108 is shown supporting only a single user device for clarity. In general, each cable modem 106 and 108 is capable of supporting a plurality of user devices for communication over the cable modem system 100. User devices may include personal computers, data terminal equipment, telephony devices, broadband media players, network-controlled appliances, or any other device capable of transmitting or receiving data over a packet-switched network.

In the example cable modem system 100, cable modem 106 represents a conventional DOCSIS-compliant cable modem. In other words, cable modem 106 transmits data packets to the CMTS 104 in formats that adhere to the protocols set forth in the DOCSIS specification. Cable modem 108 is likewise capable of transmitting data packets to the CMTS 104 in standard DOCSIS formats. However, in accordance with embodiments of the present invention, the cable modem 108 is also configured to transmit data packets to the CMTS 104 using proprietary protocols that extend beyond the DOCSIS specification. Nevertheless, cable modem 108 is fully interoperable with the DOCSIS-compliant cable modems, such as cable modem 106, and with DOCSIS-compliant CMTS equipment. The manner in which cable modem 108 operates to transfer data will be described in further detail herein.

Furthermore, in the example cable modem system 100, the CMTS 104 operates to receive and process data packets transmitted to it in accordance with the protocols set forth in the DOCSIS specification. However, in accordance with embodiments of the present invention, the CMTS 104 can also operate to receive and process data packets that are formatted using proprietary protocols that extend beyond those provided by the DOCSIS specification, such as data packets transmitted by the cable modem 108. The manner in which the CMTS 104 operates to receive and process data will also be described in further detail herein.

Figure 2:
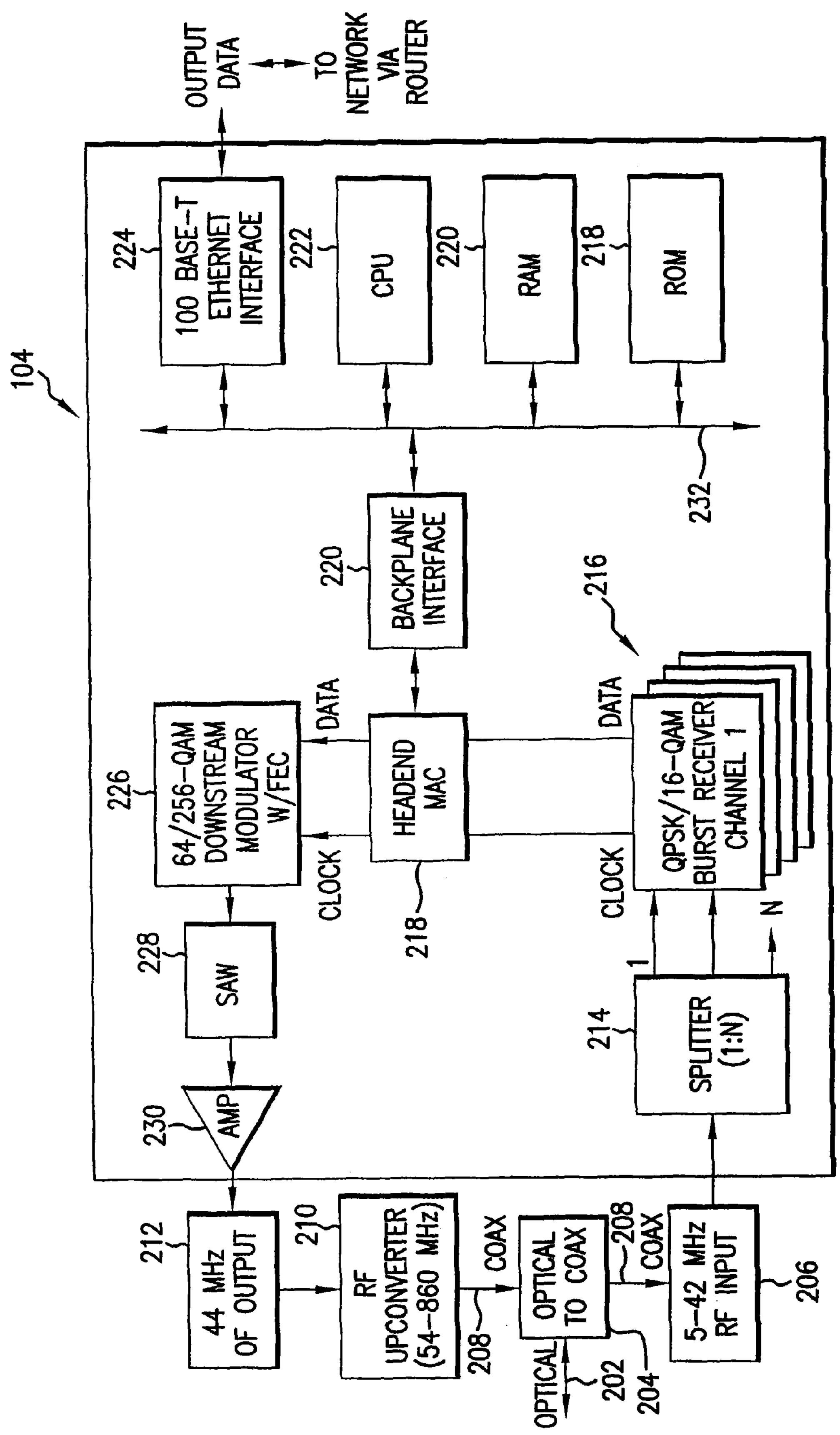
FIG. 2 is a schematic block diagram of a cable modem termination system (CMTS) in accordance with embodiments of the present invention.

B. Example Cable Modem System Components in Accordance with Embodiments of the Present Invention FIG. 2 depicts a schematic block diagram of an implementation of the CMTS 104 of cable modem system 100, which is presented by way of example, and is not intended to limit the present invention. The CMTS 104 is configured to receive and transmit signals to and from the HFC network 110, a portion of which is represented by the optical fiber 202 of FIG. 2. Accordingly, the CMTS 104 will be described in terms of a receiver portion and a transmitter portion.

The receiver portion includes an optical-to-coax stage 204, an RF input 206, a splitter 214, and a plurality of burst receivers 216. Reception begins with the receipt of upstream burst signals originating from one or more cable modems by the optical-to-coax stage 204 via the optical fiber 202. The optical-to-coax stage 204 routes the received burst signals to the radio frequency (RF) input 206 via coaxial cable 208. In embodiments, these upstream burst signals having spectral characteristics within the frequency range of roughly 5-42 MHz.

The received signals are provided by the RF input 206 to the splitter 214 of the CMTS 104, which separates the RF input signals into N separate channels. Each of the N separate channels is then provided to a separate burst receiver 216 which operates to demodulate the received signals on each channel in accordance with either a Quadrature Phase Shift Key (QPSK) or 16 Quadrature Amplitude Modulation (QAM) technique to recover the underlying information signals. Each burst receiver 216 also converts the underlying information signals from an analog form to digital form. This digital data is subsequently provided to the headend media access control (MAC) 218.

The headend MAC 218 operates to process the digital data in accordance with the DOCSIS specification and, when appropriate, in accordance with proprietary protocols that extend beyond the DOCSIS specification, as will be described in further detail herein. The functions of the headend MAC 218 may be implemented in hardware or in software. In the example implementation of FIG. 2, the functions of the headend MAC 218 are implemented both in hardware and software. Software functions of the headend MAC 218 may be stored in either the random access memory (RAM) 220 or the read-only memory (ROM) 218 and executed by the CPU 222. The headend MAC is in electrical communication with these elements via a backplane interface 220 and a shared communications medium 232. In embodiments, the shared communications medium 232 may comprise a computer bus or a multiple access data network.

The headend MAC 218 is also in electrical communication with the Ethernet interface 224 via both the backplane interface 220 and the shared communications medium 232. When appropriate, Ethernet packets recovered by the headend MAC 218 are transferred to the Ethernet interface 224 for delivery to the packet-switched network 112 via a router.

The transmitter portion of the CMTS 104 includes a downstream modulator 226, a surface acoustic wave (SAW) filter 228, an amplifier 230, an intermediate frequency (IF) output 212, a radio frequency (RF) upconverter 210 and the optical-to-coax stage 204. Transmission begins with the generation of a digital broadcast signal by the headend MAC 218. The digital broadcast signal may include data originally received from the packet-switched network 112 via the Ethernet interface 224. The headend MAC 218 outputs the digital broadcast signal to the downstream modulator 226 which converts it into an analog form and modulates it onto a carrier signal in accordance with either a 64-QAM or 256-QAM technique.

The modulated carrier signal output by the downstream modulator 256 is input to the SAW filter 228 which passes only spectral components of the signal that are within a desired bandwidth. The filtered signal is then output to an amplifier 230 which amplifies it and outputs it to the IF output 212. The IF output 212 routes the signal to the RF upconverter 210, which upconverts the signal. In embodiments, the upconverted signal has spectral characteristics in the frequency range of approximately 54-860 MHz. The upconverted signal is then output to the optical-to-coax stage 204 over the coaxial cable 208. The optical-to-coax stage 204 broadcasts the signal via the optical fiber 202 of the HFC network 110.

Figure 3:
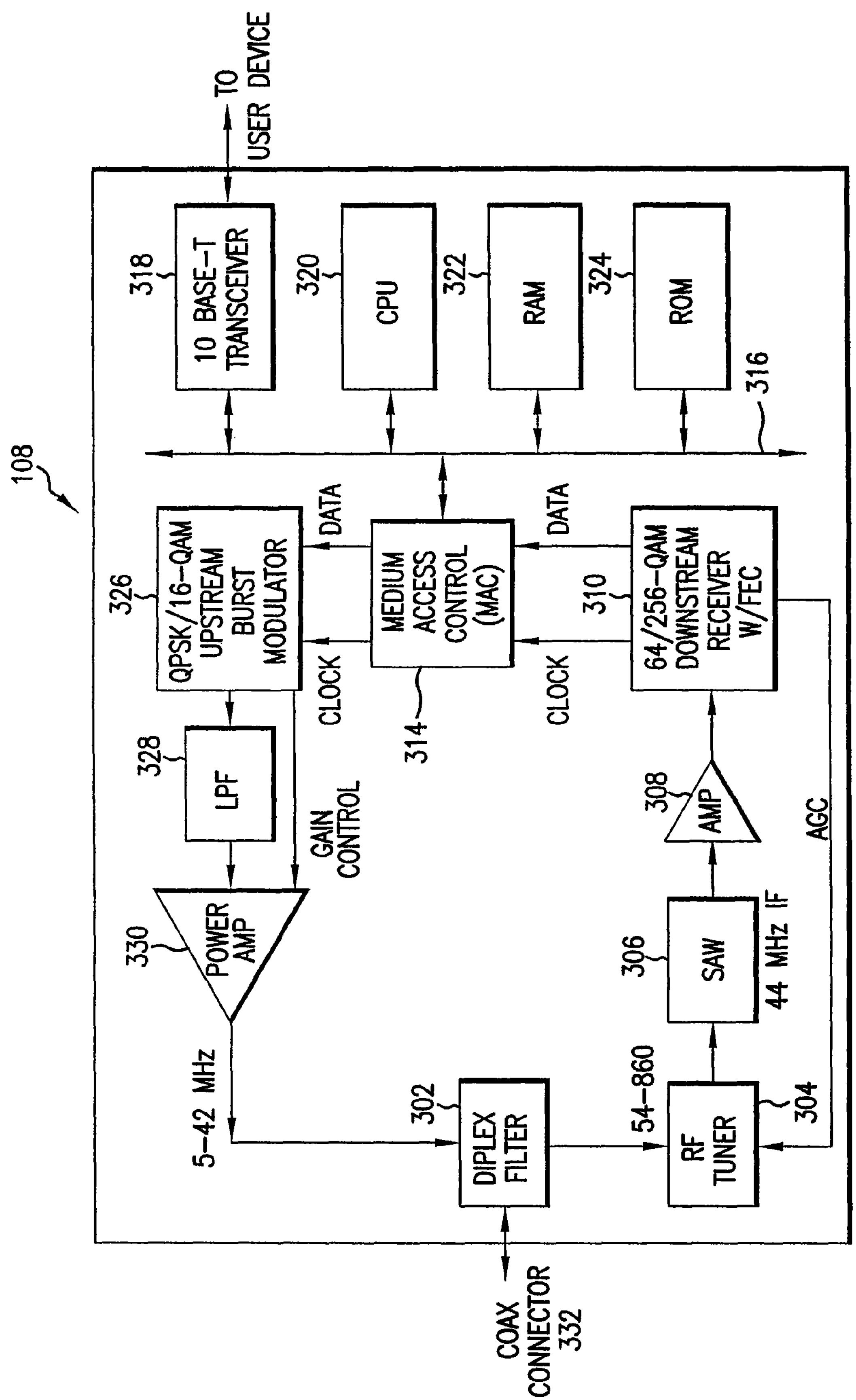
FIG. 3 is a schematic block diagram of a cable modem in accordance with embodiments of the present invention.

FIG. 3 depicts a schematic block diagram of an implementation of the cable modem 108 of cable modem system 100, which is presented by way of example, and is not intended to limit the present invention. The cable modem 108 is configured to receive and transmit signals to and from the HFC network 110 via the coaxial connector 332 of FIG. 3. Accordingly, the cable modem 108 will be described in terms of a receiver portion and a transmitter portion.

The receiver portion includes a diplex filter 302, an RF tuner 304, a SAW filter 306, an amplifier 308, and a downstream receiver 310. Reception begins with the receipt of a downstream signal originating from the CMTS 104 by the diplex filter 302. The diplex filter 302 operates to isolate the downstream signal and route it to the RF tuner 304. In embodiments, the downstream signal has spectral characteristics in the frequency range of roughly 54-860 MHz. The RF tuner 304 downconverts the signal and outputs it to the SAW filter 306, which passes only spectral components of the downconverted signal that are within a desired bandwidth. The filtered signal is output to the amplifier 308 which amplifies it and passes it to the downstream receiver 310. Automatic gain controls are provided from the downstream receiver 310 to the RF tuner 304.

The downstream receiver 310 demodulates the amplified signal in accordance with either a 64-QAM or 256-QAM technique to recover the underlying information signal. The downstream receiver 310 also converts the underlying information signal from an analog form to digital form. This digital data is subsequently provided to the media access control (MAC) 314.

The MAC 314 processes the digital data, which may include, for example, Ethernet packets for transfer to an attached user device. The functions of the MAC 314 may be implemented in hardware or in software. In the example implementation of FIG. 3, the functions of the MAC 314 are implemented in both hardware and software. Software functions of the MAC 314 may be stored in either the RAM 322 or the ROM 324 and executed by the CPU 320. The MAC 314 is in electrical communication with these elements via a shared communications medium 316. In embodiments, the shared communications medium may comprise a computer bus or a multiple access data network.

The MAC 314 is also in electrical communication with the Ethernet interface 318 via the shared communications medium 316. When appropriate, Ethernet packets recovered by the MAC 314 are transferred to the Ethernet interface 318 for transfer to an attached user device.

The transmitter portion of the cable modem 108 includes an upstream burst modulator 326, a low pass filter 328, a power amplifier 330, and the diplex filter 302. Transmission begins with the construction of a data packet by the MAC 314. The data packet may include data originally received from an attached user device via the Ethernet interface 318. In accordance with embodiments of the present invention, the MAC 314 may format the data packet in compliance with the protocols set forth in the DOCSIS specification or, when appropriate, may format the data packet in compliance with a proprietary protocol that extends beyond those set forth in the DOCSIS specification, as will be described in further detail herein. The MAC 314 outputs the data packet to the upstream burst modulator 326 which converts it into analog form and modulates it onto a carrier signal in accordance with either a QPSK or 16-QAM technique.

The upstream burst modulator 326 outputs the modulated carrier signal to the low pass filter 328 which passes signals with spectral characteristics in a desired bandwidth. In embodiments, the desired bandwidth is within the frequency range of approximately 5-42 MHz. The filtered signals are then introduced to the power amplifier 330 which amplifies the signal and provides it to the diplex filter 302. The gain in the power amplifier 330 is regulated by the burst modulator 326. The diplex filter 302 isolates the amplified signal and transmits it upstream over the HFC network 110 during a scheduled burst opportunity.

C. Supporting Extended Data Transfer Protocols in Accordance with Embodiments of the Present Invention As noted above, in accordance with embodiments of the present invention, the cable modem 108 and the CMTS 104 send and receive data, respectively, in proprietary formats that extend beyond standard DOCSIS protocols. For example, in embodiments, the cable modem 108 modifies data packets in accordance with a proprietary header suppression scheme for transmission to the CMTS 104, and, upon receipt of the modified data packets, the CMTS 104 reconstructs them in accordance with the same proprietary header compression scheme.

In further accordance with embodiments of the present invention, the cable modem 108 is nevertheless interoperable with conventional DOCSIS-compliant CMTS equipment that, unlike the CMTS 104, do not provide support for extended protocols. The cable modem 108 achieves this end by determining whether it is communicating with a CMTS that supports extended protocols, such as the CMTS 104, or with a CMTS that does not. If the CMTS does not support extended protocols, the cable modem 108 transfers data formatted in accordance with standard DOCSIS protocols rather than extended protocols.

Figure 4:
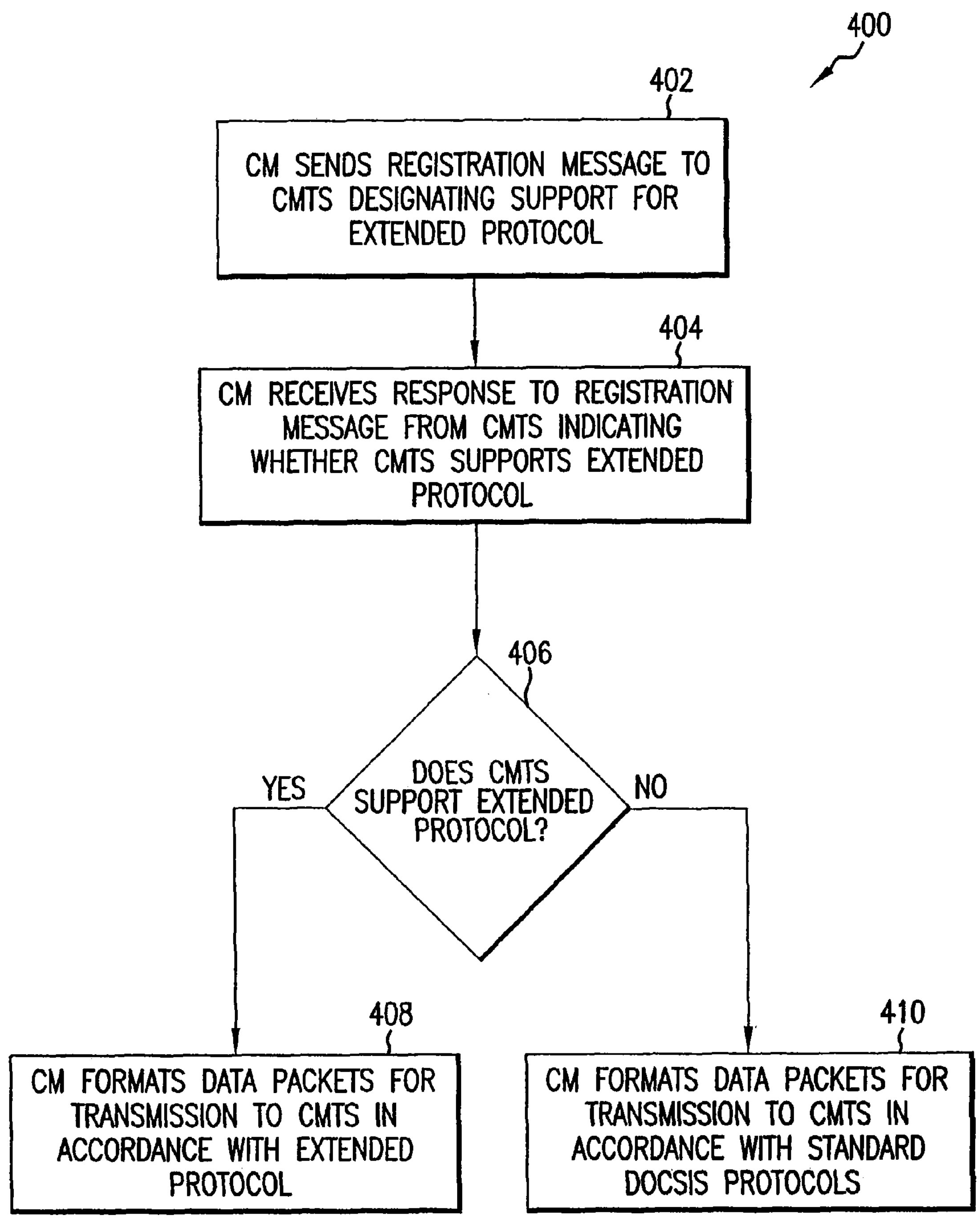
FIG. 4 is a flowchart of a method for supporting extended protocols in a cable modem system in accordance with embodiments of the present invention.

FIG. 4 depicts a flowchart 400 of a method for supporting extended protocols in a cable modem system in accordance with embodiments of the present invention that explains this process in more detail. The invention, however, is not limited to the description provided by the flowchart 400. Rather, it will be apparent to persons skilled in the relevant art(s) from the teachings provided herein that other functional flows are within the scope and spirit of the present invention. The flowchart 400 will be described with continued reference to the example CMTS 104 and cable modem 108 of the cable modem system 100, as well as in reference to the example hardware implementation of the cable modem 108 of FIG. 3. The invention, however, is not limited to those embodiments.

In step 402, the cable modem 108 sends a registration message to the CMTS 104 designating support for an extended protocol. With regard to the example implementation of cable modem 108 described in reference to FIG. 3, the MAC 314 constructs this registration message, as well as all other MAC maintenance messages issued by the cable modem 108.

In embodiments, the cable modem 108 sends this registration message as part of an exchange of registration messages that must occur between a cable modem and a CMTS when the cable modem first appears on the HFC network. In accordance with the DOCSIS specification, this exchange of registration messages generally includes the sending of a Registration Request (REG-REQ) message from the cable modem to the CMTS and the sending of a Registration Response (REG-RSP) message from the CMTS to the cable modem in response to the received REG-REQ message. This registration protocol is well-known in the art.

In embodiments, the cable modem 108 notifies the CMTS 104 that it supports an extended protocol by placing an extended protocol support descriptor in a vendor-specific information field of the REG-REQ message that it sends to the CMTS104. Conversely, in such embodiments, the absence of an extended protocol support descriptor in a vendor-specific information field of the REG-REQ message designates that a cable modem supports only standard DOCSIS protocols.

At step 404, the cable modem 108 receives a response to the registration message from the CMTS 104 that indicates whether or not the CMTS 104 supports the extended protocol. Since the CMTS 104 of the exemplary cable modem system 100 supports the same extended protocol as cable modem 108, as discussed above, the response to the registration message will indicate that the extended protocol is supported. However, if the CMTS 104 did not support the extended protocol (for example, if it was a conventional DOCSIS-compliant CMTS), then the response to the registration message would include an indication that the CMTS 104 failed to recognize the extended protocol. For example, in embodiments where the registration message comprises a REG-REQ message that includes an extended protocol support descriptor in a vendor-specific information field, the response may be a REG-RSP message that indicates that the CMTS 104 failed to recognize extended protocol support descriptor.

If the response to the registration message indicates that the extended protocol is supported by the CMTS, then the cable modem 108 will format data packets for transmission to the CMTS in accordance with the extended protocol, as shown by steps 406 and 408. If, on the other hand, the response to the registration message indicates that the CMTS does not support the extended protocol, then the cable modem 108 will format data packets for transmission to the CMTS in accordance with standard DOCSIS protocols, as shown by steps 406 and 410. As discussed above in regard to the example implementation of cable modem 108 depicted in FIG. 3, the MAC 314 is responsible for formatting data packets for transmission to the CMTS.

In alternate embodiments of the present invention, a private communications channel may be utilized to implement steps 402 and 404 of flowchart 400 instead of the standard DOCSIS REG-REQ, REG-RSP protocol described above. For example, in such an embodiment, the CMTS 104 sends a unicast UDP message to the cable modem 108 following successful cable modem registration that indicates that the CMTS 104 is capable of supporting extended protocols (step not shown in FIG. 4). If the cable modem 108 supports an extended protocol, it responds to the UDP message by sending a UDP response indicating which extended protocol it supports. In accordance with this technique, the registration message of step 402 comprises the UDP response from the cable modem 108. In embodiments, the UDP response also indicates the specific degree to which the cable modem 108 is capable of supporting the extended protocol.

If the cable modem does not support an extended protocol, it sends no response to the UDP message. In embodiments, the CMTS 104 re-transmits the UDP message a predetermined number of times and, if no response is received from the cable modem after the predetermined number of re-transmissions, the CMTS 104 determines that the cable modem does not support any extended protocols. However, if the CMTS 104 receives an appropriate UDP response from the cable modem 108, it captures the extended protocol capabilities of the cable modem 108 and responds with a second UDP message indicating whether or not it supports the specific extended protocol supported by the cable modem 108. In accordance with this technique, the response to the registration message of step 404 comprises the second UDP message from the CMTS 104.

The method described in flowchart 400 ensures interoperability between a cable modem that supports an extended protocol in accordance with embodiments of the present invention and CMTS equipment that does not support the same protocol. Similarly, a CMTS that supports an extended protocol in accordance with embodiments of the present invention, such as CMTS 104, is interoperable with a cable modem that does not support the same extended protocol. For example, the CMTS 104 is interoperable with conventional DOCSIS-compliant cable modems that do not support extended protocols, such as cable modem 106. The CMTS 104 achieves this end by determining whether a received packet has been sent from a conventional DOCSIS-compliant cable modem, such as the cable modem 106, or from a cable modem capable of transmitting data using extended protocols, such as the cable modem 108, and processing the packet accordingly.

Figure 5:
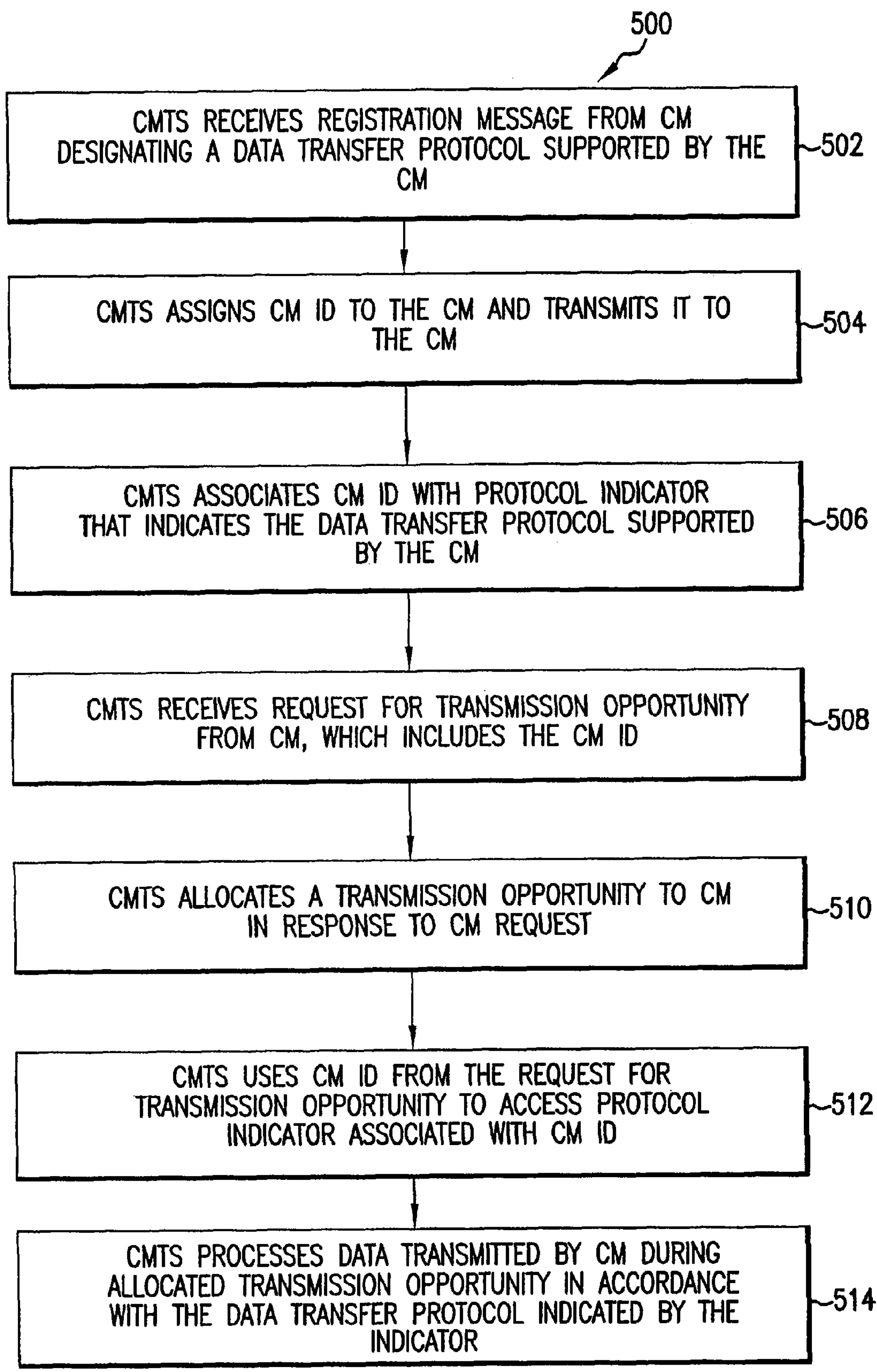
FIG. 5 is a flowchart of a method for supporting extended protocols in a cable modem system in accordance with embodiments of the present invention.

FIG. 5 depicts a flowchart 500 of a method for supporting extended protocols in a cable modem system in accordance with embodiments of the present invention that explains this process in more detail. The invention, however, is not limited to the description provided by the flowchart 500. Rather, it will be apparent to persons skilled in the relevant art(s) from the teachings provided herein that other functional flows are within the scope and spirit of the present invention. The flowchart 500 will be described with continued reference to the example CMTS 104 and cable modems 106 an 108 of the cable modem system 100, as well as in reference to the example hardware implementation of the CMTS 104 of FIG. 2. The invention, however, is not limited to those embodiments.

At step 502, the CMTS 104 receives a registration message from a cable modem designating a data transfer protocol supported by the cable modem. With regard to the example cable modem system 100 of FIG. 1, the registration message may be from cable modem 106, in which case the message designates data transfer in accordance with standard DOCSIS protocols, or the registration message may be from cable modem 108, in which case the message designates data transfer in accordance with an extended protocol. In embodiments, the registration message is a DOCSIS REG-REQ message, and the presence of an extended protocol descriptor in a vendor-specific field of the REG-REQ message designates data transfer in accordance with an extended protocol, while the absence of the extended protocol descriptor designates data transfer in accordance with standard DOCSIS protocols.

At step 504, the CMTS 104 assigns a unique cable modem ID to the cable modem and transmits the cable modem ID to the cable modem. In embodiments, the cable modem ID comprises the DOCSIS primary Service ID (SID) that is assigned by the CMTS and transmitted to the cable modem as part of the DOCSIS REG-RSP message. With regard to the example implementation of CMTS 104 described in reference to FIG. 2, the headend MAC 218 is responsible for assigning a unique cable modem ID to the cable modem.

At step 506, the CMTS 104 creates an association in memory between the cable modem ID and a protocol indicator that indicates the data transfer protocol supported by the cable modem. With regard to the example implementation of CMTS 104 described in reference to FIG. 2, this task is carried out by the headend MAC 218 which stores the cable modem ID and protocol indicator as associated values in either ROM 218 or RAM 220. In embodiments, the CMTS 104 stores the cable modem ID and protocol indicator as associated values in a look-up table.

At step 508, the CMTS 104 receives a request for transmission opportunity from a cable modem which includes the cable modem ID associated with the cable modem. In embodiments, the request is received in a request contention area defined by a DOCSIS allocation MAP. The allocation MAP is a varying-length MAC Management message transmitted by the CMTS on the downstream channel that describes, for some time interval, the uses to which the upstream bandwidth must be put. The allocation MAP allocates bandwidth in terms of basic time units called mini-slots. A given allocation MAP may describe some mini-slots as a grant for a particular cable modem to transmit data in and other mini-slots as available for contention transmission by multiple cable modems. The DOCSIS allocation MAP is described in the DOCSIS specification and is well-known in the art.

At step 510, the CMTS 104 allocates a transmission opportunity to the cable modem in response to the request for transmission opportunity. In embodiments, the CMTS 104 allocates a transmission opportunity to the cable modem by assigning a number of mini-slots in a DOCSIS allocation MAP to the cable modem for transferring data upstream, in accordance with the DOCSIS specification. With regard to the example implementation of CMTS 104 described in reference to FIG. 2, the construction of a MAP allocation message is executed by the headend MAC 218.

At step 512, the CMTS 104 uses the cable modem ID from the request for transmission opportunity to access the protocol indicator associated with the cable modem ID, which was stored in memory at prior step 506. In embodiments, the CMTS 104 consults a look-up table that maps the cable modem ID to the protocol indicator. In regard to the example implementation of CMTS 104 described in reference to FIG. 2, this step is performed by the headend MAC 218.

At step 514, the CMTS 104 processes data transmitted by the cable modem during the allocated transmission opportunity in accordance with the data transfer protocol indicated by the indicator. For example, if the indicator indicates that an extended protocol is supported, as in the case of cable modem 108, then the CMTS 104 will process the data packet it expects to receive from the cable modem in accordance with an extended protocol. If no support for an extended protocol is indicated, as in the case of cable modem 106, then the CMTS 104 will process the data packet it expects to receive from the cable modem in accordance with standard DOCSIS procotols. In regard to the example implementation of CMTS 104 described in reference to FIG. 2, the processing of data packets is performed by the headend MAC 218.

Thus, in accordance with embodiments of the present invention, the CMTS 104 acquires and stores information during cable modem registration about the capabilities of the cable modems to which it will communicate. When the CMTS 104 subsequently allocates upstream bandwidth to a cable modem, it accesses the stored information to determine how to process the data it expects to receive from the cable modem. This technique is facilitated by the TDMA aspects of a cable modem system, which requires the CMTS to be aware of which cable modem it is receiving data from at any given time. This technique is advantageous because it permits the use of protocols that extend beyond DOCSIS, while ensuring interoperability by adhering to standard DOCSIS registration, request and grant protocols.

1. Packet Header Suppression

FIGS. 6A-8 are useful for explaining a manner in which packets are compressed by cable modem 108 and expanded by the CMTS 104 in accordance with embodiments of the present invention.

Figure 6A:
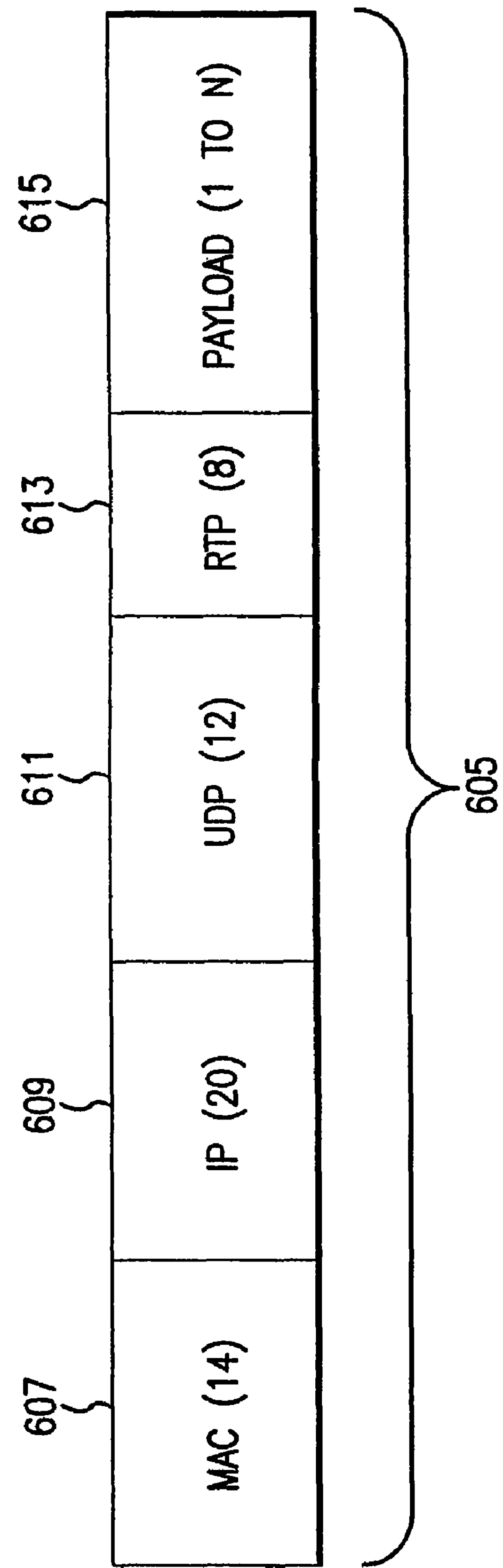
FIG. 6A is a block diagram of an uncompressed packet typically received by a cable modem in accordance with embodiments of the present invention.

FIG. 6A represents a data packet 605 generated by a user device for transmission over the HFC network 110. The data packet 605 includes a MAC header 607, an IP header 609, a UDP header 611, an RTP header 613, and a Payload 615. In this example, the MAC header 607 comprises 14 bytes, the IP header 609 comprises 20 bytes, the UDP header 611 comprises 12 bytes, the RTP header 613 comprises 8 bytes, and the Payload 615 comprises anywhere from 1 to N bytes, depending on the type of data being sent.

In accordance with the present invention, the data packet 605 can be generated by an application program running on the user device 116 described above in reference to FIG. 1. For example, an application program running on the user device 116 may generate voice or data information for transmission over the HFC network 110. This voice or data information comprises the payload 615 of the data packet 605. The application program running on the user device 116 will append the IP header 609, the UDP header 611, and the RTP header 613 to the payload 615 to allow for transmission in accordance with standard IP protocols. An Ethernet card within the user device 116 will further append the MAC header 607 to the data packet 605 to allow for transmission in accordance with standard Ethernet protocols.

Upon receiving data packet 605, the cable modem suppresses the data packet 605 in accordance with any desired header suppression technique. Examples of header suppression techniques include standard DOCSIS PHS, as well as techniques that extend beyond standard DOCSIS protocols, such as Dynamic Delta Encoding and RTP Encoding, descriptions of which are provided in further detail herein. After reading this specification, one skilled in the relevant art(s) would recognize that any number of suppression techniques may be utilized without departing from the scope of the present invention.

Figure 6B:
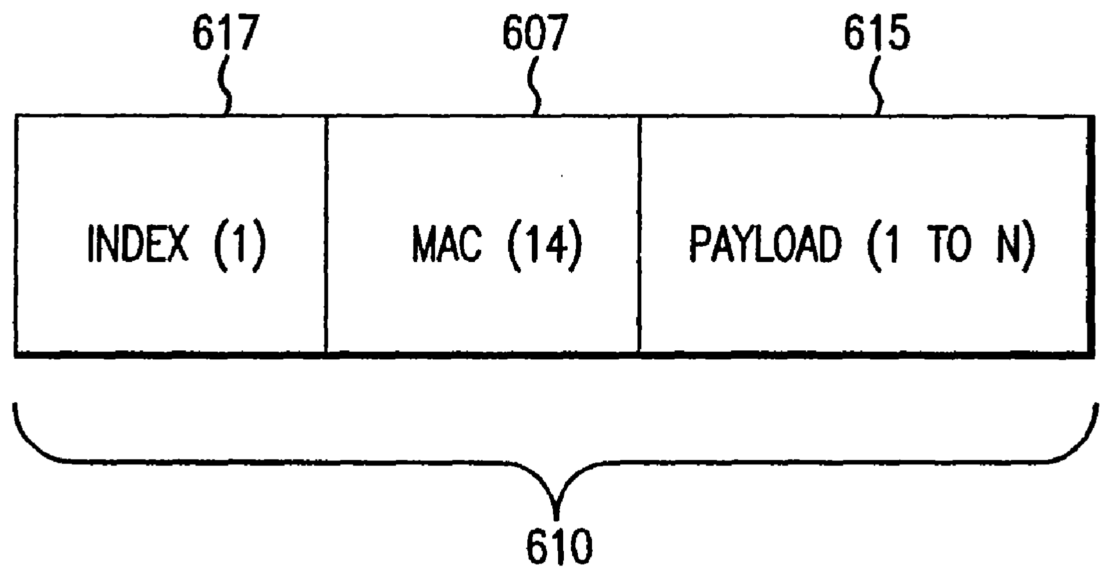
FIG. 6B is a block diagram of a packet compressed by a cable modem in accordance with embodiments of the present invention.

FIG. 6B represents the appearance of data packet 605 after being compressed to produce a compressed data packet 610 in accordance with embodiments of the present invention. In this exemplary embodiment, the IP header 609, the UPD header 611, and the RTP header 613 are eliminated and replaced with a single byte index 617. Accordingly, the compressed data packet 610 is comprised of Index 617, MAC header 607, and Payload 615. The index 617 is comprised of one byte and is used to indicate that data packet 610 has been compressed. The index 617 is also used to indicate the particular suppression technique used to compress the data packet. Further details of index 617 will be described below with respect to FIG. 7. As a result of eliminating the above specified headers, the compressed data packet 610 is 40 bytes smaller than the original data packet 605.

Figure 6C:
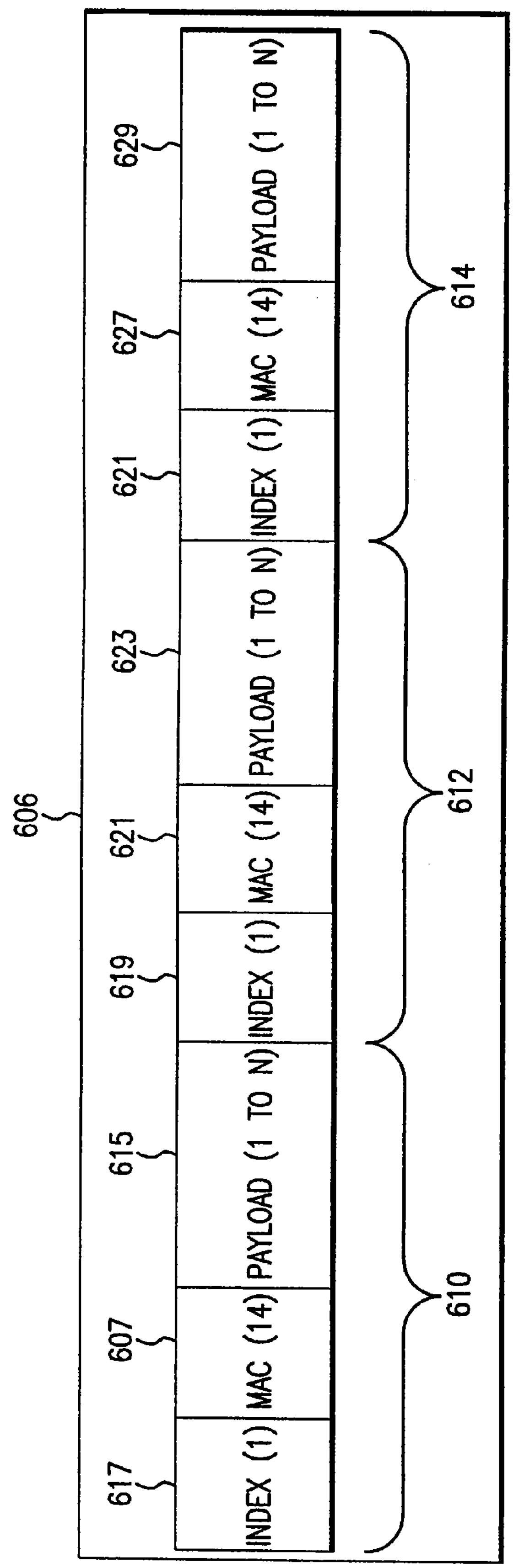
FIG. 6C is a block diagram of a single SID containing multiple packets compressed by a cable modem using different packet header suppression techniques in accordance with embodiments of the present invention.

FIG. 6C is an example of a mixed protocol DOCSIS transmit burst (i.e., SID) 606 that contains multiple packets suppressed in accordance with embodiments of the present invention. The mixed protocol SID 606 is comprised of the compressed data packet 610 and additional compressed data packets 612 and 614. In one embodiment, compressed data packet 610 is compressed using DOCSIS PHS as indicated by the index 617. Compressed data packet 612 is compressed using Dynamic Delta encoding as indicated by the index 619, and compressed data packet 614 is compressed using RTP encoding as indicated by the index 621. The indices 617, 619, and 621 separate the packets within the mixed protocol SID 606. This separation is, in effect, a framing protocol. In this way, the mixed protocol SID 606 is able to transmit multiple packets suppressed by different packet header suppression techniques.

Figure 7:
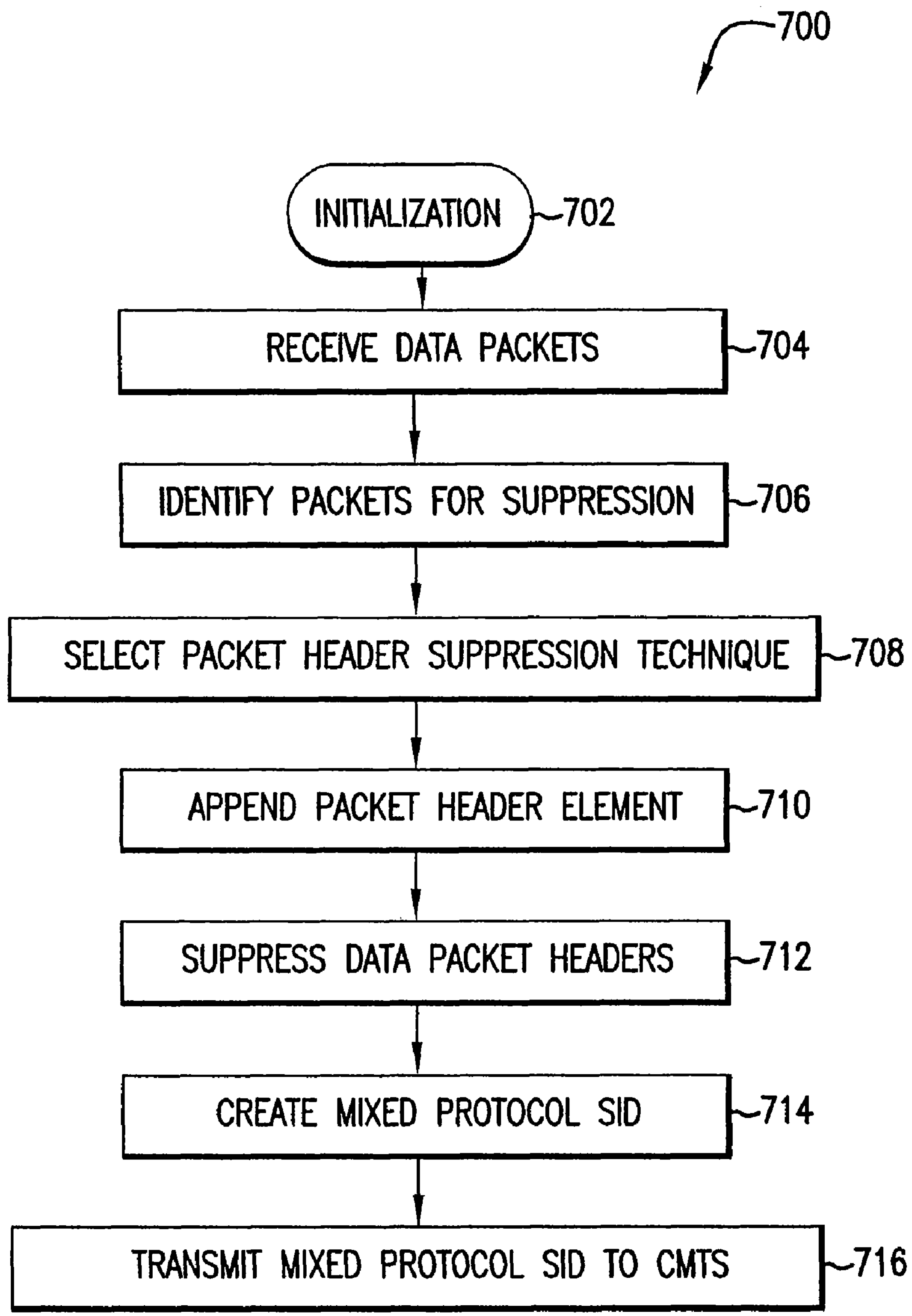
FIG. 7 is a flowchart of a method for compressing packets using different packet header suppression techniques in accordance with embodiments of the present invention.

FIG. 7 depicts a flowchart 700 of a method for compressing packets using different packet header suppression techniques in accordance with embodiments of the present invention. The invention, however, is not limited to the description provided herein with respect to flowchart 700. Rather, it will be apparent to persons skilled in the relevant art(s) after reading the teachings provided herein that other functional flows are within the scope and spirit of the present invention. The flowchart 700 will be described with continued reference to the example cable modem system 100 of FIG. 1.

At step 702, the cable modem 108 is turned on and initiates a handshaking routine with the CMTS 104 via the HFC network 110. During this initialization process, the cable modem 108 designates one or more index numbers to represent a particular type of packet header suppression technique. For example, index 1 might be designated for DOCSIS PHS suppression, while index numbers 2 thru 10 might be designated for use with dynamic delta encoding. Still further, index numbers 11 thru 20 might be designated for use with RTP encoding. Once these designations are made, this information is communicated to the CMTS 104 via the HFC network 110. During the initialization process, the rules associated with suppressing and expanding a packet in accordance with the available suppression techniques are also exchanged. The rules are provided to the CMTS 104 by the cable modem 108. The CMTS 104 stores the index numbers and their corresponding rules in a lookup table for subsequent retrieval during the packet expansion process.

In embodiments, the above-described initialization process is part of standard DOCSIS cable modem registration protocols. In alternate embodiments, a private communication channel previously described in reference to FIG. 4, above, may be used to facilitate the transfer of index numbers and rules. This may be particularly advantageous in DOCSIS 1.0 cable modem systems in which the DOCSIS protocol does not define any classification/header suppression capability.

At step 704, the cable modem 108 receives a data packet from the user device 116. The data packet may be, for example, data packet 605 of FIG. 6A.

At step 706, the cable modem 108 determines if the data packet should be suppressed in accordance with the present invention. In an embodiment, the cable modem 108 will not suppress the data packet if it is an uncompressible packet (i.e., not an IP packet). In this case, the cable modem 108 would transmit the data packet with its full header.

At step 708, the cable modem 108 will select an appropriate packet header suppression technique for those data packets identified in step 706. In an embodiment, where data packets are of the unknown IP datagram type, DOCSIS PHS is selected. For IP/RTP data packets (i.e., voice packets), RTP suppression is selected. For IP/TCP variable length data packets, Dynamic Delta suppression is selected.

At step 710, the cable modem 108 will append a packet header element to the data packet being suppressed. The packet header element contains the index number designated in step 702 for the particular suppression technique selected in step 708.

At step 712, the data packet is suppressed in accordance with the rules associated with the suppression technique selected in step 708. The resulting compressed data packet may be for example, the compressed data packet 610 of FIG. 6B. In accordance with the present invention, the steps (704-712) allow for the suppression of data packets in accordance with any desired header suppression technique. The index number associated with each data packet identifies the beginning of the data packet. Accordingly, the index number is a useful mechanism for separating one data packet from another and identifying the particular header suppression technique used to process each data packet.

As previously discussed, the DOCSIS protocol enables concatenation of data packets but, it does not allow the mixing of different header suppression techniques within a single DOCSIS transmit burst or SID. However, because the index number contained in the packet header element appended in step 710 provides a means for separating the packets, the mixing of different header suppression techniques within a SID is now possible. Accordingly, in an alternative embodiment, a mixed protocol SID is produced in step 714.

In step 714, the data packets are concatenated with one another. As a result of concatenating packets suppressed with different header suppression techniques, the SID can now be viewed as a mixed protocol SID. In effect, the index serves as a framing protocol that separates the packets within the mixed protocol SID as well as communicates the type of header suppression used on each data packet within the mixed protocol SID. In an embodiment, the mixed protocol SID can be for example, the mixed protocol SID 606 of FIG. 6C. Finally, in step 716, the mixed protocol SID is transmitted to a CMTS 104.

2. Packet Header Expansion

Figure 8:
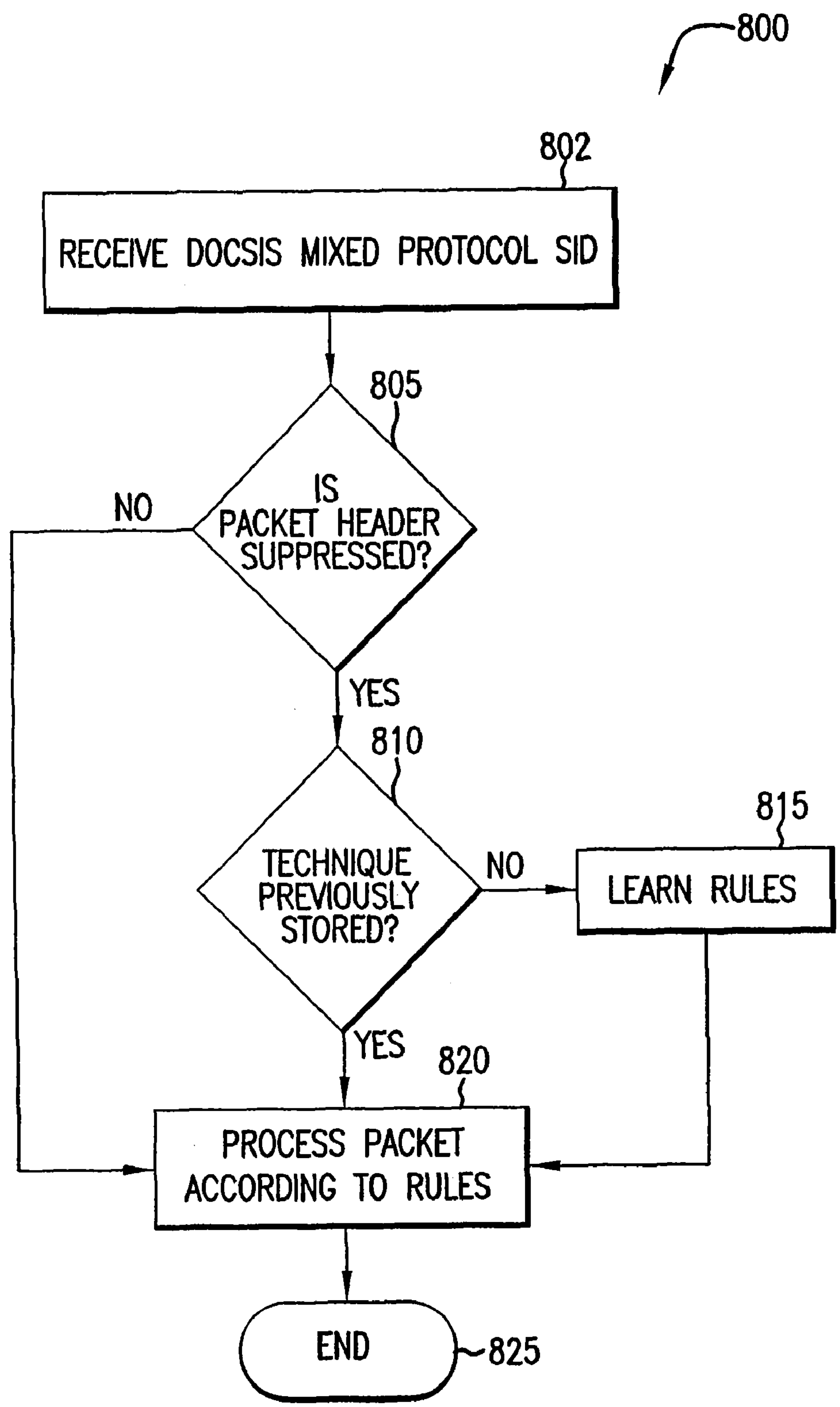
FIG. 8 is a flowchart of a method for expanding packets compressed using different packet header suppression techniques in accordance with embodiments of the present invention.

FIG. 8 is a flowchart of a method for expanding packets compressed using different packet header suppression techniques in accordance with embodiments of the present invention.

At step 802, the CMTS 104 receives a mixed protocol SID comprised of one or more data packets.

At step 805, the CMTS 104 examines each of the data packets to determine if it has been suppressed. If a packet header element has been appended to a data packet, then the CMTS 104 knows that the data packet has been suppressed. If no packet header element is found, then the data packet has not been suppressed and controls passes immediately to step 820.

At step 810, the CMTS 104 searches its lookup table for the index number contained in the packet header element. If the index number is found then the expansion rules associated with the suppression technique have been previously provided to the CMTS 104. In an embodiment, the expansion rules would have been previously provided during the initialization process described in step 702. If the index number is not found, then control passes to step 815.

At step 815, the CMTS 104 and the cable modem 108 exchange data describing the rules for expanding the data packet in real time (i.e., as the data packet arrives).

At step 820, the CMTS 104 processes each of the data packets. In the case where the data packet is not suppressed (i.e., a packet header element was not present) the data packet is processed according to standard DOCSIS protocols. In the case where the data packet is suppressed (i.e., a packet header element was present) the CMTS 104 retrieves the rules for expanding the data packet based upon the suppression technique indicated by the index number found in the packet header element. In expanding the data packet, CMTS 104 produces an uncompressed data packet. In an embodiment, at the end of step 820, CMTS 104 would produce a data packet such as uncompressed data packet 605 of FIG. 6A. Because the mixed protocol SID contains one or more data packets, steps 805 thru 820 are repeated until all the data packets within the mixed protocol SID have been processed. Processing ends at step 825.

3. RTP Header Suppression

As previously stated, the invention provides for Real-time Transport Protocol (RTP) header suppression. The RTP header suppression technique of the present invention provides great efficiency gains in network bandwidth utilization by eliminating the transmission of redundant patterns and by suppressing changing fields in a data stream. The invention accomplishes this by recognizing regular patterns in network traffic. In embodiments, the regular patterns may be eliminated by having a sender of network traffic, such as CM 108, and a receiver of network traffic, such as CMTS 104, agree on the rules for proper header reconstruction in order to reproduce the header at the receiving end. By reducing the amount of network bandwidth needed to transmit RTP information across the network, the present invention enables increased performance for the same number of users on the network, as well as the ability to efficiently add more users to the network.

Figure 9A:
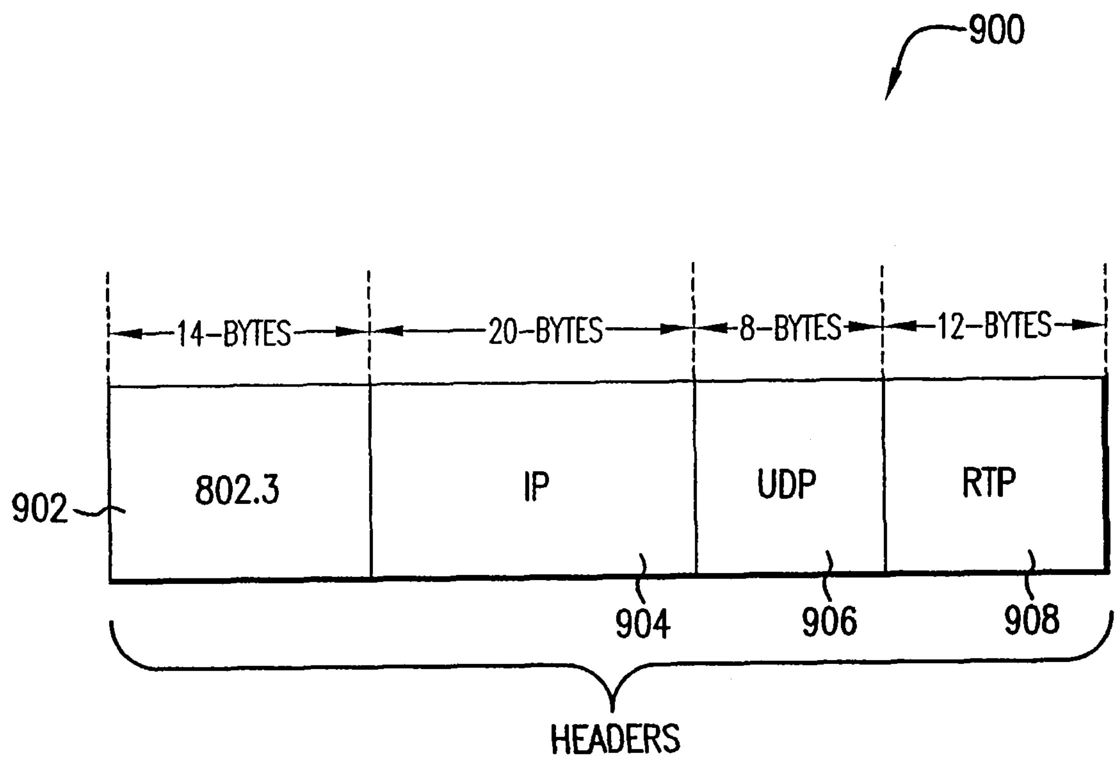
FIG. 9A is a diagram of an exemplary 802.3/IP/UDP/RTP header.

Prior to describing the RTP header suppression technique of the invention, a conventional 802.3/IP/UDP/RTP protocol header 900 for an RTP transmission will be described in FIG. 9A. Exemplary protocol header 900 includes a 14-byte 802.3 header 902, a 20-byte IP (Internet Protocol) header 904, an 8-byte UDP (User Datagram Protocol) header 906, and a 12-byte RTP header 908. In this example, 802.3/IP/UDP/RTP header 900 creates a 54-byte header. The data portion of an RTP packet may be small in comparison to the overhead required to send the data using 802.3/IP/UDP/RTP header 900. For example, the data portion of an RTP packet may be as small as 20 bytes, resulting in less than half the size of header 900. Also, most of the fields within protocol header 900 do not change from packet to packet. The transmission of such redundant patterns (non-changing header information from packet to packet) may waste large amounts of network bandwidth, especially when the data portion of the RTP packet is smaller than header 900. It would therefore be very inefficient to transmit header 900 without compressing it.

DOCSIS 1.1 enables the suppression of redundant information in packets with a feature called "payload header suppression" (PHS). PHS enables the suppression of unchanging bytes in an individual SID (i.e., data stream). Unfortunately, as previously stated, PHS cannot suppress dynamically changing fields.

Figure 9B:
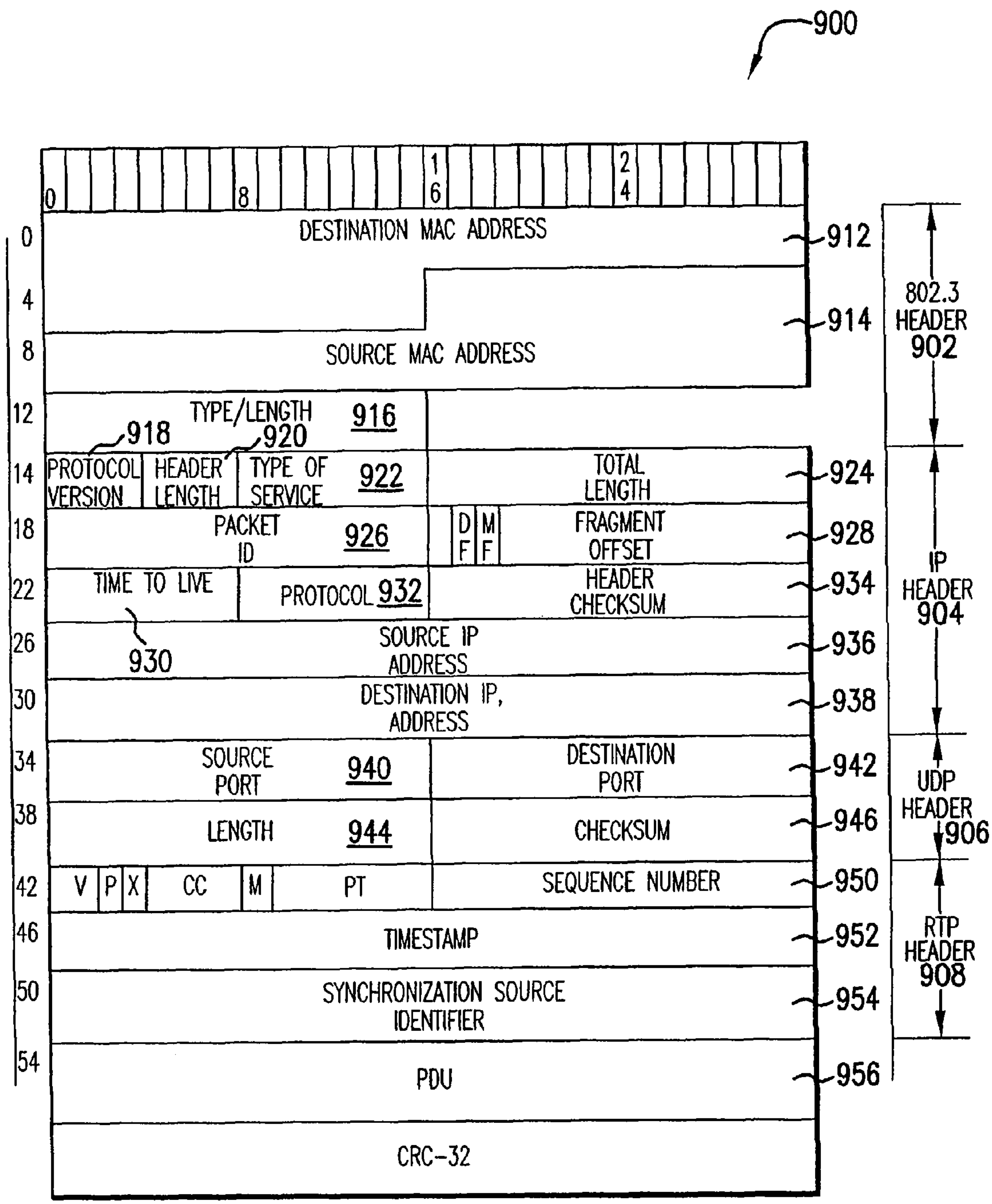
FIG. 9B is a diagram of an RTP protocol packet.

The RTP header suppression technique of the present invention increases the efficiency of data delivery by recognizing patterns of behavior in the changing fields of 802.3/IP/UDP/RTP header 900. FIG. 9B is a diagram of an RTP protocol packet 910. RTP protocol packet 910 comprises, inter alia, a destination MAC address field 912, a source MAC address field 914, a type/length field 916, a protocol version field 918, a header length field 920, a type of service field 922, a total length field 924, a packet ID field 926, a fragment offset field 928, a time to live field 930, a protocol field 932, a header checksum field 934, a source IP address field 936, a destination IP address field 938, a source port field 940, a destination port field 942, a length field 944, a checksum field 946, a flag field 948, a sequence number field 950, a timestamp field 952, a synchronization source identifier field 954, a PDU 956, and a CRC-32 958. RTP protocol packets are well known in the relevant art(s), thus, each individual field will not be discussed in detail.

Most of header 900 may be suppressed. The fields of data packet 910 that may change from packet to packet include IP Packet ID field 926, IP Header Checksum field 934, RTP sequence number field 950, and RTP timestamp field 952. UDP checksum field 946 is always set to zero because it is not used. The remaining fields remain constant for the life of a voice connection.

RTP sequence number field 950 starts at some arbitrary value and increments by a value of one for each successive packet. RTP timestamp field 952 increments by a value based on the quantization interval of the codec. The second order delta of this number will always be zero for any given codec at a given quantization interval.

The invention enables the in-order deliver of packets on the upstream DOCSIS RF link. The invention suppresses 802.3/IP/UDP/RTP header 900 on CM 108, and ensures that header 900 is recreated by CMTS 104. The reconstruction of header 900 must be an exact reconstruction. This is accomplished by calculating the difference between an RTP input packet's RTP sequence number field 950 and the previous RTP packet's RTP sequence number field 950. When the difference between successive RTP packet sequence number fields 950 is 1, the difference between a new RTP packet's timestamp field 952 and a previous RTP packet's timestamp field 952 will be the first order difference, which will appear on every successive packet while the codec and quantization interval remain constant.

By observation, it was determined that the first order difference in RTP packet timestamp field 952 is 80 decimal for a 10 millisecond quantization, for G711, G726, G738, and G729. For 5 millisecond quantization, the first order difference in RTP packet timestamp field 952 is 40 decimal.

Initially, CM 108 sends one or more unsuppressed full headers with a control bit indicating that CMTS 104 is to "learn" header 900. Once the quantization value is determined, the quantization value is used to verify Gthat the reconstruction of header 900 will be correct. At that time, CM 108 sends either a "learn header" control bit with a full header in the event that reconstruction of header 900 may be incorrect, or a 5-bit RTP sequence delta, an 8-bit quantization value, and an optional 1-byte IP packet ID delta in place of 54-byte 802.3/IP/UDP/RTP header 900. In embodiments, during the learning process, more than one sequential header may be sent with the learn bit set. This ensures that in the event a packet is dropped on the RF link, CMTS 104 will end up with a valid template header from which to recreate packets once the learn bit is no longer set.

Figure 10:
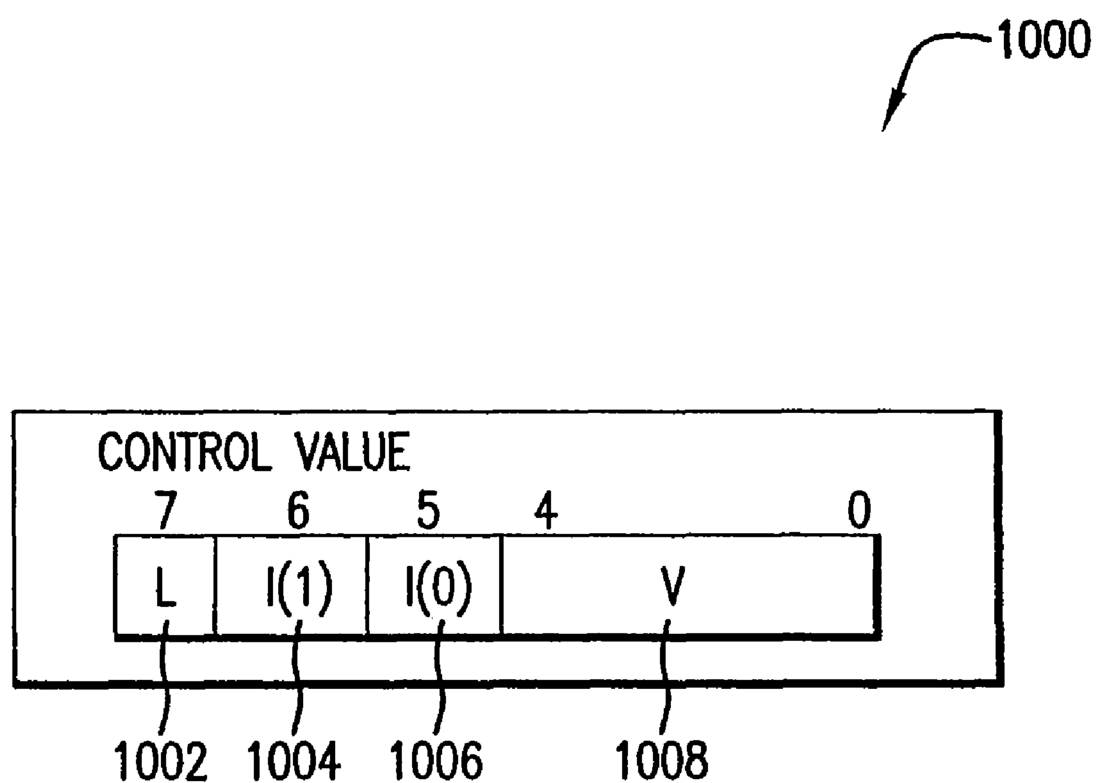
FIG. 10 is a diagram illustrating a control value byte used during the operation of a RTP header suppression technique.

FIG. 10 is a diagram illustrating a control value byte 1000 that is used during the operation of the RTP header suppression technique. Control value byte 1000 comprises an L bit 1002, an I(1) bit 1004, an I(0) bit 1006, and a 5-bit V value 1008. L bit 1002 is a learn bit. L bit 1002 is set when CMTS 104 is to learn header 900.

Modem IP protocol stacks often increment IP packet ID field 926 by either 0x0001 or 0x0100 between datagrams. The present invention uses a two-bit flag value, I(1) bit 1004 and I(0) bit 1006 to determine whether to increment IP packet ID field 926 by 0x0001 or by 0x0100 or whether to replace IP packet ID field 926 with a 2-byte delta field transmitted upstream by CM 108. If both I(1) and I(0) are not set, then IP packet ID field 926 is incremented by 0x0001. If both I(1) and I(0) are set, then IP packet ID field 926 is not incremented. If I(1) is not set and I(0) is set, then IP packet ID field 926 is incremented by 0x0100. If I(1) is set and I(0) is not set, then the change in IP packet ID field 926 is transmitted upstream in a two-byte delta field. Table 1 represents the four possibilities for determining the value of IP packet ID field 926.

TABLE 1

| I(1) | I(0) | IP packet ID |
|---|---|---|
| 0 | 0 | increment by 0x0001 |
| 0 | 1 | increment by 0x0100 |
| 1 | 0 | change is transmitted upstream in a two byte delta field |
| 1 | 1 | no increment value |

Control value (V) 1008 is a five bit value representing the delta value of sequence number field 950.

Figure 11:
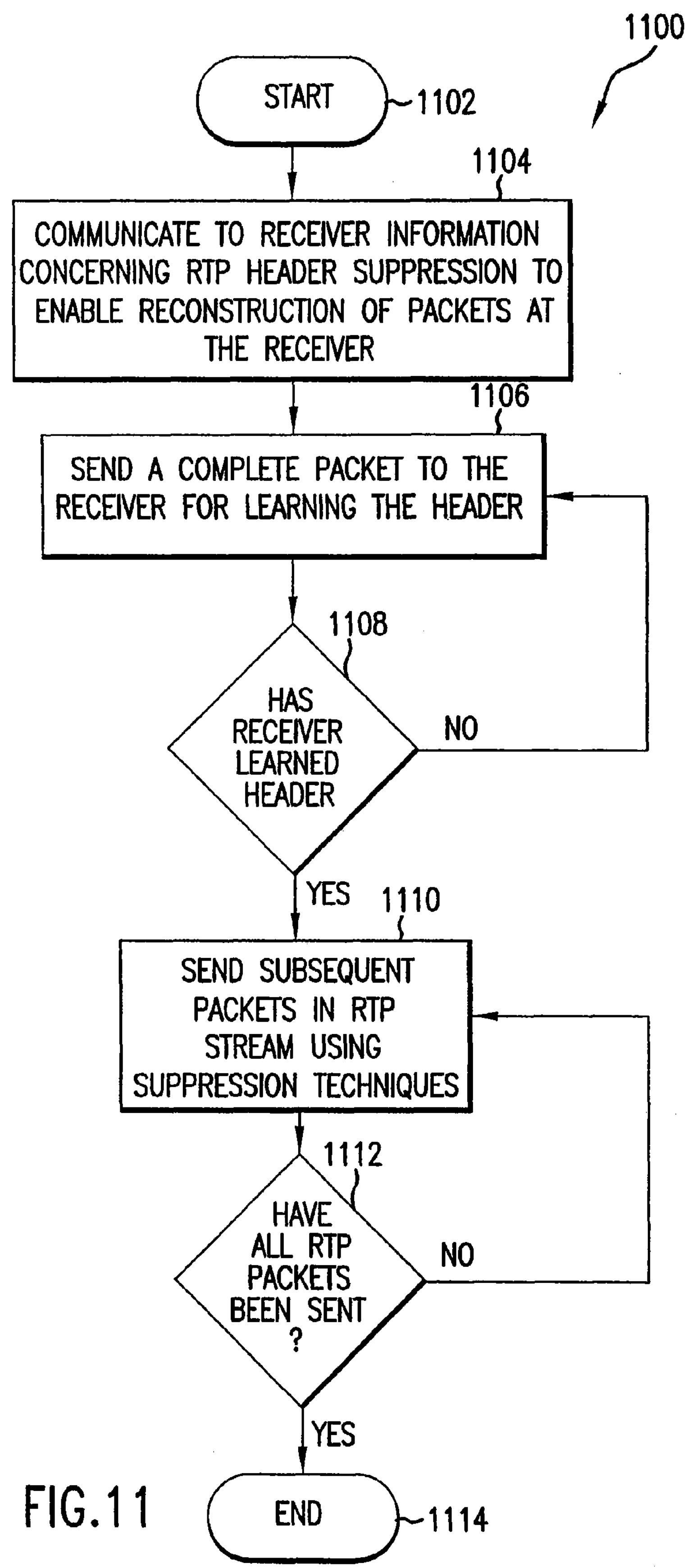
FIG. 11 is a high level flow diagram illustrating a method for RTP header suppression.

FIG. 11 is a high level flow diagram 1100 illustrating a method for RTP header suppression. The invention is not limited to the description provided herein with respect to flow diagram 1100. Rather, it will be apparent to persons skilled in the relevant art(s) after reading the teachings provided herein that other functional flow diagrams are within the scope of the present invention. The process begins with step 1102, where the process immediately proceeds to step 1104.

In step 1104, information concerning RTP header suppression is communicated from CM 108 to CMTS 104 to enable reconstruction of RTP packets at CMTS 104. As previously discussed, this may include an index number indicating the particular type of packet header suppression technique, the rules associated with suppressing and reconstructing a packet in accordance with the particular type of packet header suppression technique, etc. The process then proceeds to step 1106.

In step 1106, a complete RTP packet, such as RTP packet 910, is sent by CM 108 to CMTS 104 to enable CMTS 104 for learning. CMTS 104 stores the full header of RTP packet 910 for future reference as a template. The process then proceeds to decision step 1108.

In decision step 1108, it is determined whether CMTS 104 has learned RTP packet 910. If CMTS 104 has not learned RTP packet 910, then the process returns to step 1106, where a complete packet is sent from CM 108 to CMTS 104 for continued learning.

Returning to decision step 1108, if it is determined that CMTS 104 has learned RTP packet 910, then the process proceeds to step 1110. In step 1110, subsequent packets in the RTP stream are sent from CM 108 to CMTS 104. The subsequent packets are comprised of delta values representing changes in RTP header 900. Thus, the entire RTP packet 910 is no longer sent. Instead, only delta values representing the changes in RTP header 900 are sent. PDU field 956 is also sent. If error recovery is desired, the subsequent packets will also include an additional byte indicating the lower byte of RTP sequence number field 940. If a packet is dropped for any reason, CMTS 104 may effectively re-synchronize the header restoration algorithm by applying the changes to sequence number field 940 and timestamp field 952 of RTP header 900 for any missing packets. Thus, sending the lower order byte of packet sequence number field 940 will enable reconstruction of dropped or lost packets. The process then proceeds to decision step 1112.

In decision step 1112, it is determined whether all RTP packets have been sent. If all RTP packets have not been sent, the process returns to decision step 1110 for enabling subsequent packets in the RTP stream to be sent to CMTS 104.

Returning to decision step 1112, if it is determined that all RTP packets have been sent, then the process proceeds to step 1114, where the process ends.

Figure 12A:
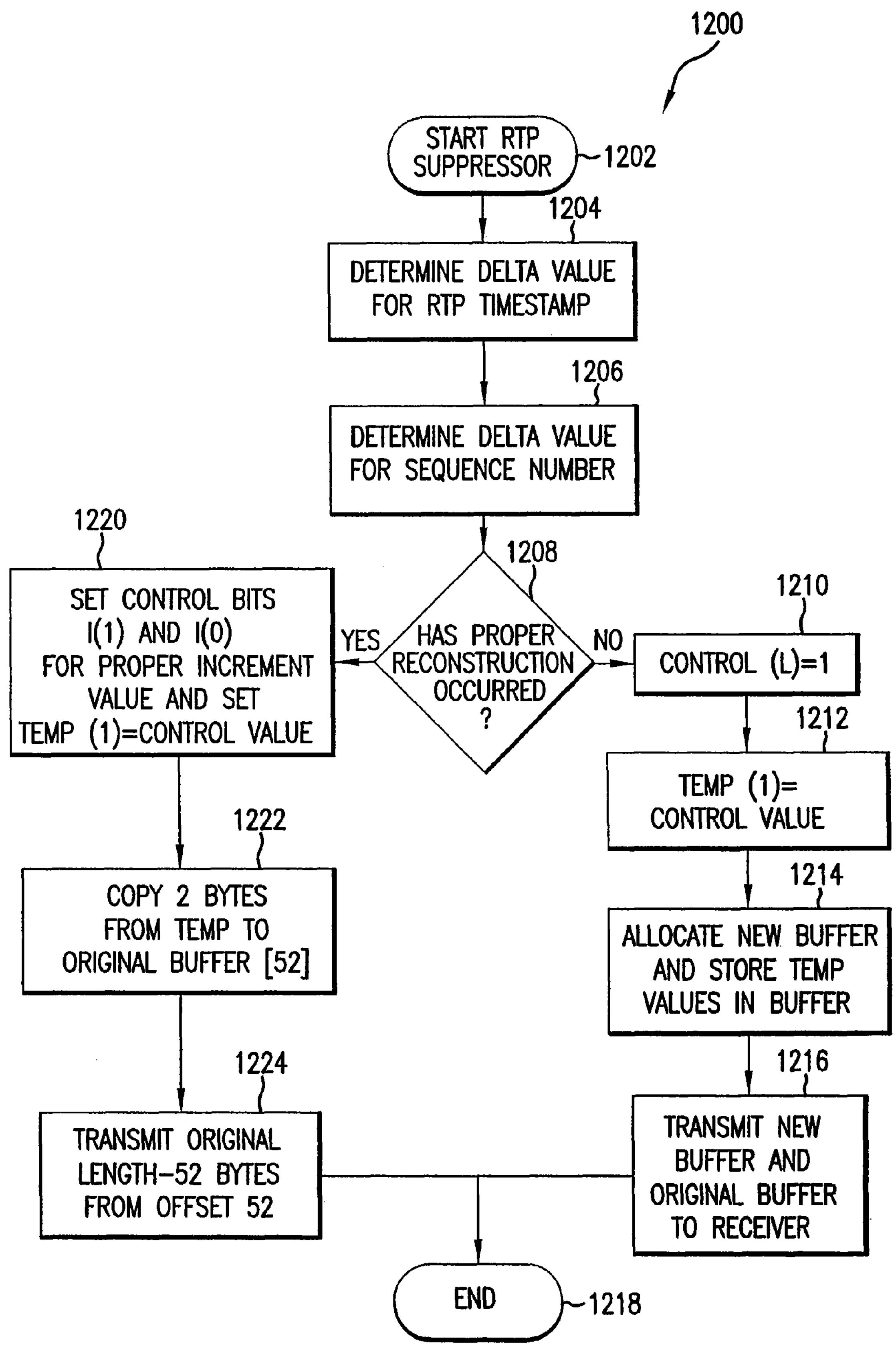
FIG. 12A is a flow diagram illustrating a method for suppressing an RTP header using an RTP header suppression technique according to an embodiment of the present invention.

FIG. 12A is a flow diagram illustrating a method for suppressing an RTP header using an RTP header suppression technique according to an embodiment of the present invention. The invention is not limited to the description provided herein with respect to flow diagram 1200. Rather, it will be apparent to persons skilled in the relevant art(s) after reading the teachings provided herein that other functional flow diagrams are within the scope of the present invention. The process begins with step 1202, where an RTP suppressor is started at the transmitting end (i.e., CM 108). The process immediately proceeds to step 1204.

In step 1204, the delta of RTP timestamp field 952 between two consecutive RTP packets 900 is determined. The resultant value is the timestamp delta value. The resultant timestamp delta value is set equal to temp(0). Note that during initialization, temp(0) is set to zero. The process then proceeds to step 1206.

In step 1206, the delta value for sequence number field 940 is determined. The resultant delta value is set equal to control value (V). This is accomplished by determining the low order byte of a new sequence number field 950 ANDed with the hex value 7f and determining the low order byte of the old sequence number field 950 ANDed with the hex value 7f. The resultant new sequence number field 950 value is then subtracted from the resultant old sequence number field 950 to obtain the delta or value of control value (V). The process then proceeds to decision step 1208.

In decision step 1208, it is determined whether proper reconstruction will occur. This is accomplished by multiplying the delta value of sequence number field 950, calculated in step 1206, by the constant value for the codec and adding it to the previous timestamp value. If this value is not equal to the new timestamp, then the process proceeds to step 1210.

In step 1210, learn bit 1002 of control value 1000 is set. The process then proceeds to step 1212.

In step 1212, temp(1) is set equal to control value 1000. Temp (1) now contains the delta value for sequence number field 950. The process then proceeds to step 1214.

In step 1214, a new buffer is allocated and the two bytes from temp (the delta value for timestamp field 952 and control value 1000, which includes the delta value for sequence number field 950) are stored in the new buffer. The process proceeds to step 1216.

In step 1216, the new buffer and the original buffer, which contains a complete RTP header 910, are transmitted to CMTS 104. Thus, the complete RTP header 910 along with the delta value for timestamp field 952 and control value 1000 are sent to CMTS 104. The process then proceeds to step 1218, where the process ends.

Returning to decision step 1208, if it is determined that the calculated value is equal to the new timestamp field 952, then CM 108 has determined the quantization value. The process proceeds to step 1220.

In step 1220, the increment value for incrementing IP packet ID field 926 is determined. Bits I(1) 1004 and I(0) 1006 of control value 1000 are set according to the value of the increment for the IP protocol stack being used. The control value is then stored in temp(1). The process then proceeds to step 1222.

In step 1222, the two bytes from temp are copied to the original buffer. Temp (0) is the delta value for timestamp field 952 or the quantization value. Temp (1) is control value 1000, which includes the delta value for sequence number field 950. The process then proceeds to step 1224.

In step 1224, the original length minus 52 bytes starting at offset 52 is transmitted. Thus, the quantization value or the delta of timestamp field 952, control value 1000, and PDU field 956 are transmitted to CMTS 104. The process then proceeds to step 1218, where the process ends.

Figure 12B:
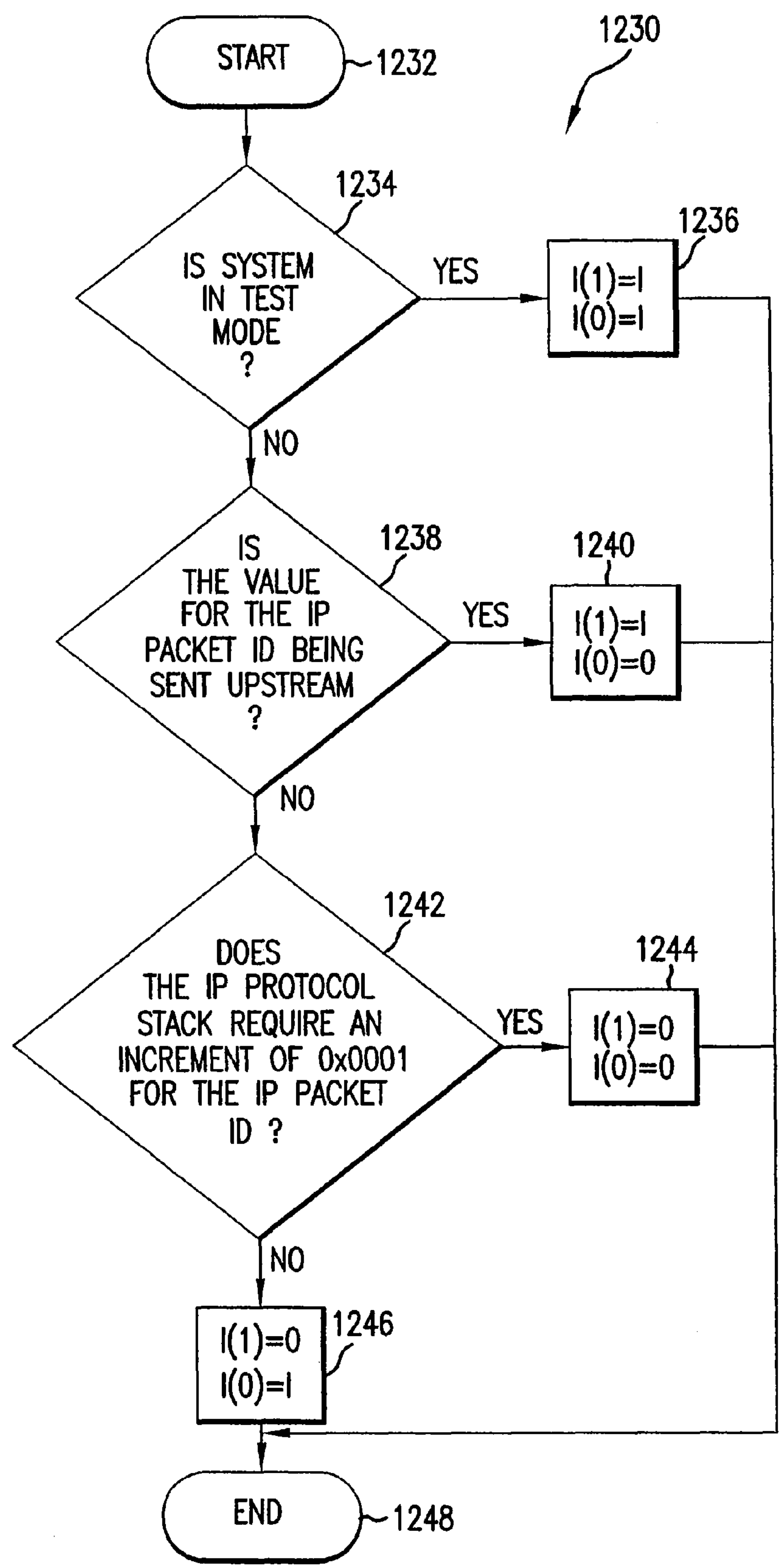
FIG. 12B is a flow diagram illustrating a method for setting the increment of an IP packet ID field in an RTP header according to an embodiment of the present invention.

As previously stated, modem IP protocol stacks commonly increment IP packet ID field 926 by either 0x0001 or 0x01000 between datagrams. A special rule in the present invention handles the setting of control bits 1004 and 1006 to determine the increment value. FIG. 12B is a flow diagram illustrating a method for setting increment bits I(1) 1004 and I(0) 1006 of control value 1000 for incrementing IP packet ID field 926 in RTP packet 910. The process begins in step 1232, where the process immediately proceeds to decision step 1234.

The present invention incorporates a test mode in which testing of various aspects of the system may be done. When certain tests are performed, control bits I(1) 1004 and I(0) 1006 are set accordingly to provide an increment of zero. In decision step 1234, it is determined whether the system is in a test mode. If the system is in a test mode, then the process proceeds to step 1236.

In step 1236, control value bit I(1) 1004 is set to 1 and control value bit I(0) 1006 is set to 1. The process then proceeds to step 1248.

Returning to decision step 1234, if it is determined that the system is not in a test mode, then the process proceeds to decision step 1238.

In decision step 1238, it is determined whether the value for IP packet ID field 926 is to be sent upstream. If the value for IP packet ID field 926 is to be sent upstream, the process will proceed to step 1240.

In step 1240, control value bit I(1) 1004 is set to 1 and control value bit I(0) 1006 is set to 0. The process then proceeds to step 1248.

Returning to decision step 1238, if the value for IP packet ID field 926 is not being sent upstream, the process proceeds to decision step 1242.

In decision step 1242, it is determined whether the IP protocol stack requires an increment of 0x0001 for IP packet ID field 926. If the IP protocol stack does require an increment of 0x0001 for IP packet ID field 926, then the process proceeds to step 1244.

In step 1244, control value bit I(1) 1004 is set to 0 and control value bit I(0) 1006 is set to 0. The process then proceeds to step 1248.

Returning to decision step 1242, if the IP protocol stack does not require an increment of 0x0001 for IP packet ID field 926, then the process proceeds to 1246.

In step 1246, an increment of 0x0100 is needed for IP packet ID field 926. Control value bit I(1) 1004 is set to 0 and control value bit I(0) 1006 is set to 1. The process then proceeds to step 1248.

In step 1248, the process ends.

Figure 13:
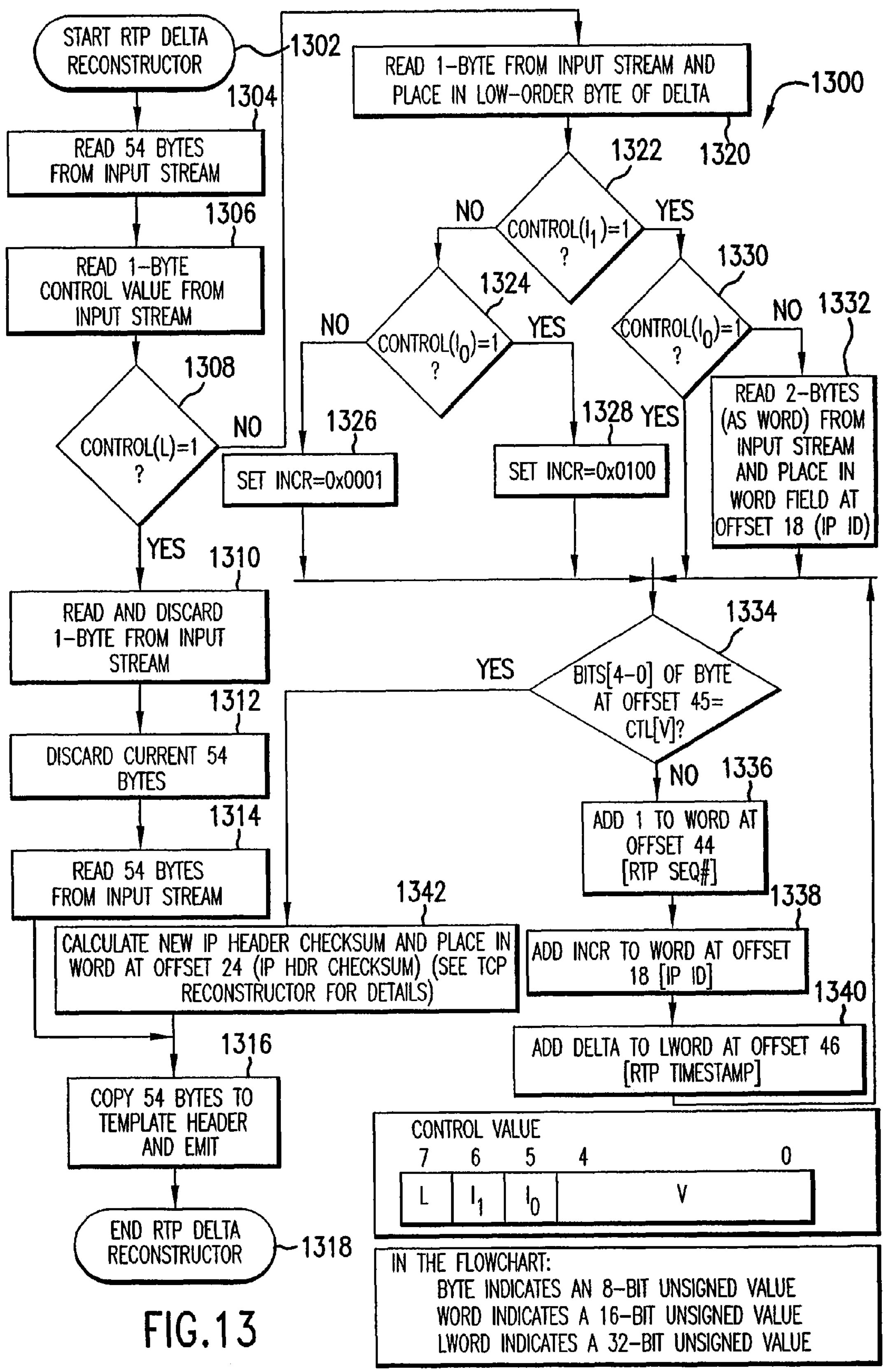
FIG. 13 is a flow diagram illustrating a method for reconstructing an RTP header using an RTP header suppression technique according to an embodiment of the present invention.

FIG. 13 is a flow diagram 1300 illustrating a method for reconstruction of a suppressed RTP packet according to an embodiment of the present invention. The invention is not limited to the description provided herein with respect to flow diagram 1300. Rather, it will be apparent to persons skilled in the relevant art(s) after reading the teachings provided herein that other functional flow diagrams are within the scope of the present invention. The process begins with step 1302, where the reconstructor is started. The process then proceeds to step 1304.

In step 1304, a 54-byte header is read. The process then proceeds to step 1306.

In step 1306, 1-byte control value 1000 is read from the input stream. The process then proceeds to decision step 1308.

In decision step 1308, it is determined whether learn bit 1002 of control value 1000 is set. If it is determined that learn bit 1002 is set, then header 900 needs to be learned by CMTS 104. The process then proceeds to step 1310.

In step 1310, a second 1-byte value is read from the input stream. This second 1-byte value is discarded. The process then proceeds to step 1312.

In step 1312, the current 54-byte header that was read in step 1304 is discarded. CMTS 104 discards this data because this 54-byte header was generated by the hardware's payload header suppression mechanism at the end of the reconstructor process, which will be discussed below with reference to step 1318. When the hardware's payload header suppression mechanism injects this 54-byte header, the 54-byte header is placed prior to control value 1000. Thus, when learn bit 1002 is set, this 54-byte header is considered garbage and must be discarded. From the point of view of CM 108, what was sent was a suppression index. Receipt of the suppression index by CMTS 104 caused CMTS 104 to inject 54-bytes of incorrect data into the data stream. The process then proceeds to step 1314.

In step 1314, the correct 54-byte header, transmitted from CM 108, is read from the input stream. The process then proceeds to step 1316.

In step 1316, the 54-byte header is copied to a template header and the 54-byte header followed by the data from PDU 956 is emitted. The process then proceeds to step 1318, where the process ends.

Returning to decision step 1308, if it is determined that learn bit 1002 of control value 1000 is not set, then the process proceeds to step 1320.

In step 1320, the second 1-byte value from the input stream is read and placed into a low-order byte of a local variable named DELTA. DELTA is a 32-bit long word. DELTA is pre-initialized to zero at the start of RTP delta reconstructor process 1300. The process then proceeds to step 1322.

Step 1322 begins the process for determining whether to increment IP packet ID field 926 as set forth in Table 1. In step 1322, it is determined whether I(1) 1004 of control value 1000 is set. If I(1) 1004 of control value 1000 is not set, then the process proceeds to step 1324.

In step 1324, it is determined whether I(0) 1006 of control value 1000 is set. If I(0) is not set, then the process proceeds to step 1326.

In step 1326, a local variable named INCR is set to 0x0001 for incrementing IP packet ID field 926. Note that local variable INCR is a 16-bit unsigned value. INCR is pre-initialized to zero at step 1302. The process then proceeds to step 1334.

Returning to step 1324, if I(0) is set, the process proceeds to step 1328. In step 1328, local variable INCR is set to 0x0100 for incrementing IP packet ID field 926. The process then proceeds to step 1334.

Returning to step 1322, if I(1) is set, the process proceeds to step 1330. In step 1330, it is determined whether I(0) 1006 of control value 1000 is set. If I(0) is set, then the process proceeds to step 1334.

Returning to step 1330, if I(0) is not set, then the process proceeds to step 1332. In step 1332, the change in IP packet ID field 926 is transmitted upstream from CM 108. A two-byte unsigned value is read in from the input stream and placed at offset 18 of the reconstructed data packet. Offset 18 of the reconstructed data packet is IP packet ID field 926. The process then proceeds to step 1334.

Steps 1334 through 1340 provide all of the updates to IP packet ID field 926, RTP sequence number field 950, and RTP timestamp field 952 for the reconstruction of RTP packet 910. In step 1334, it is determined whether the bits 4-0 of the byte at offset 45 (low-order bits of sequence number field 950) of RTP packet 910 are equal to V 1008 in control value 1000. If it is determined that the bits 4-0 of the byte at offset 45 (low-order bits of sequence number field 950) of RTP packet 910 are equal to V 1008 in control value 1000, then the process proceeds to step 1342.

In step 1342, a new IP header checksum is determined and placed at offset 24 (IP header checksum 934). IP header checksum field 934 is the 16-bit one's complement of the one's complement sum of all 16-bit words in header 900. For purposes of computing the checksum, the value of the checksum field is zero.

Returning to step 1334, if it is determined that the bits 4-0 of the byte at offset 45 (low-order bits of sequence number field 950) of RTP packet 910 are not equal to V 1008 in control value 1000, then the process proceeds to step 1336.

In step 1336, the value of one is added to the word at offset 44 of RTP packet 910, which is RTP sequence number field 950. The process then proceeds to step 1338.

In step 1338, the word at offset 18 of RTP packet 910, which is IP packet ID field 926, is incremented by local variable INCR. The process then proceeds to step 1340.

In step 1340, the word at offset 46 of RTP packet 910, which is RTP timestamp field 952, is incremented by local variable DELTA. The process then returns to step 1334, to determine if control value (V) 1008 matches the five low-order bits in the sequence number field 950 of RTP packet 910. Steps 1334 through 1340 will be repeated until these numbers are equal. When these numbers are equal, the process will proceed to step 1342 as described above.

4. Dynamic Delta Encoding Scheme

As previously stated, the invention provides for optimizing the transmission of TCP/IP (Internet Protocol) traffic across a DOCSIS network. The suppression technique of the present invention is field oriented rather than byte oriented. Many fields in a TCP protocol header do not change between packets in the same TCP connection stream. This redundant information is transmitted once, and suppressed in subsequent packets. Other fields in the TCP protocol header change in a predictable manner. These fields are not transmitted in their entirety. Instead, a smaller delta encoded value is transmitted that represents each field's change in value from one packet to the next. The delta-encoded values for 32-bit fields are always represented as a 16-bit number. This technique reduces the bandwidth required to send the changing fields by approximately 50%, and thus, provides a high efficiency gain in TCP Acknowledgement (ACK) transmission.

DOCSIS cable modems can ensure in-order delivery of packets on each IP stream. This guaranteed order of delivery enables the use of delta encoded fields to update any changing fields in a 802.3/IP/TCP protocol header.

Figure 14A:
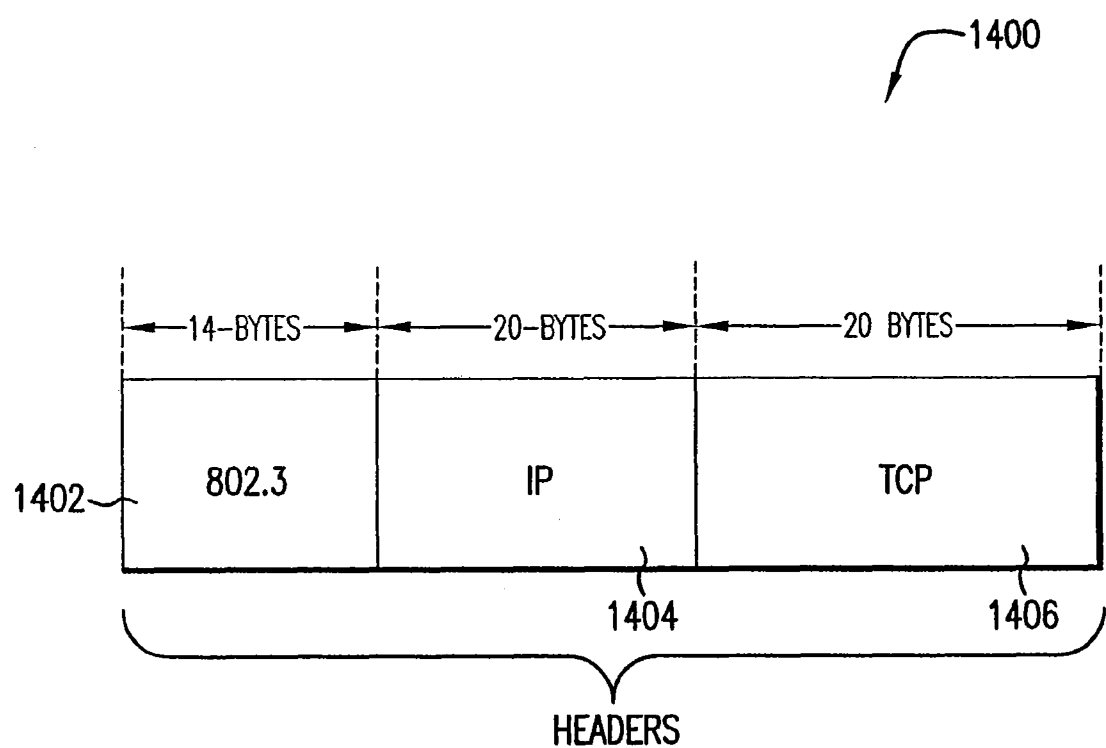
FIG. 14A is a diagram illustrating an exemplary 802.3/IP/TCP header.

Prior to describing the dynamic delta encoding scheme for TCP header suppression, a conventional 802.3/IP/TCP protocol header 1400 for TCP/IP transmission will be described in FIG. 14A. Protocol header 1400 includes a 14-byte 802.3 header 1402, a 20-byte IP header 1404, and a 20-byte TCP header 1406. In this example, 802.3/IP/TCP header 1400 creates a 54-byte header for TCP/IP transmission.

Figure 14B:
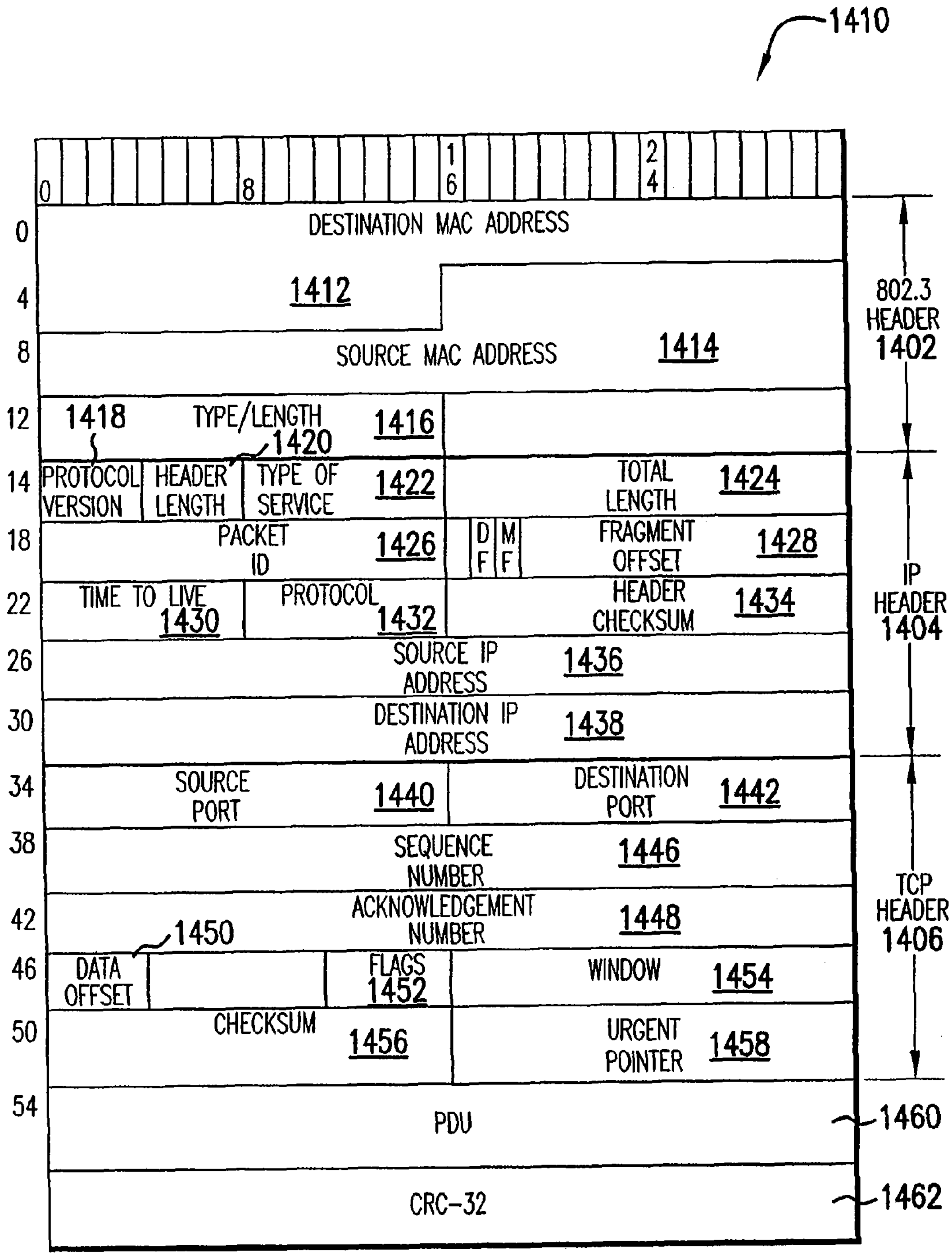
FIG. 14B is a diagram illustrating a TCP Protocol packet.

FIG. 14B is a diagram of a TCP protocol packet 1410. TCP protocol packet 1410 comprises, inter alia, a destination MAC address field 1412, a source MAC address field 1414, a type/length field 1416, a protocol version field 1418, a header length field 1420, a type of service field 1422, a total length field 1424, a packet ID field 1426, a fragment offset field 1428, a time to live field 1430, a protocol field 1432, a header checksum field 1434, a source IP address field 1436, a destination IP address field 1438, a source port field 1440, a destination port field 1442, a sequence number field 1446, an acknowledgement number field 1448, a data offset field 1450, a flags field 1452, a window field 1454, a checksum field 1456, an urgent pointer field 1458, a PDU field 1460, and a CRC-32 field 1462. TCP protocol packets are well known in the relevant art(s), thus, each individual field will not be discussed in detail.

Most of the fields in TCP protocol packet 1410 do not change between packets in the same TCP connection stream. In TCP protocol packet 1410, all of header 1402 and most of header 1404 may be suppressed once the receiver has learned the redundant or non-changing fields. Many of the fields in TCP header 1406 change between packets in the same TCP connection stream. With the present invention, these fields are not transmitted in their entirety. Instead, a smaller delta encoded value is transmitted. The delta encoded value represents each field's change in value from one packet to the next.

Figure 15:
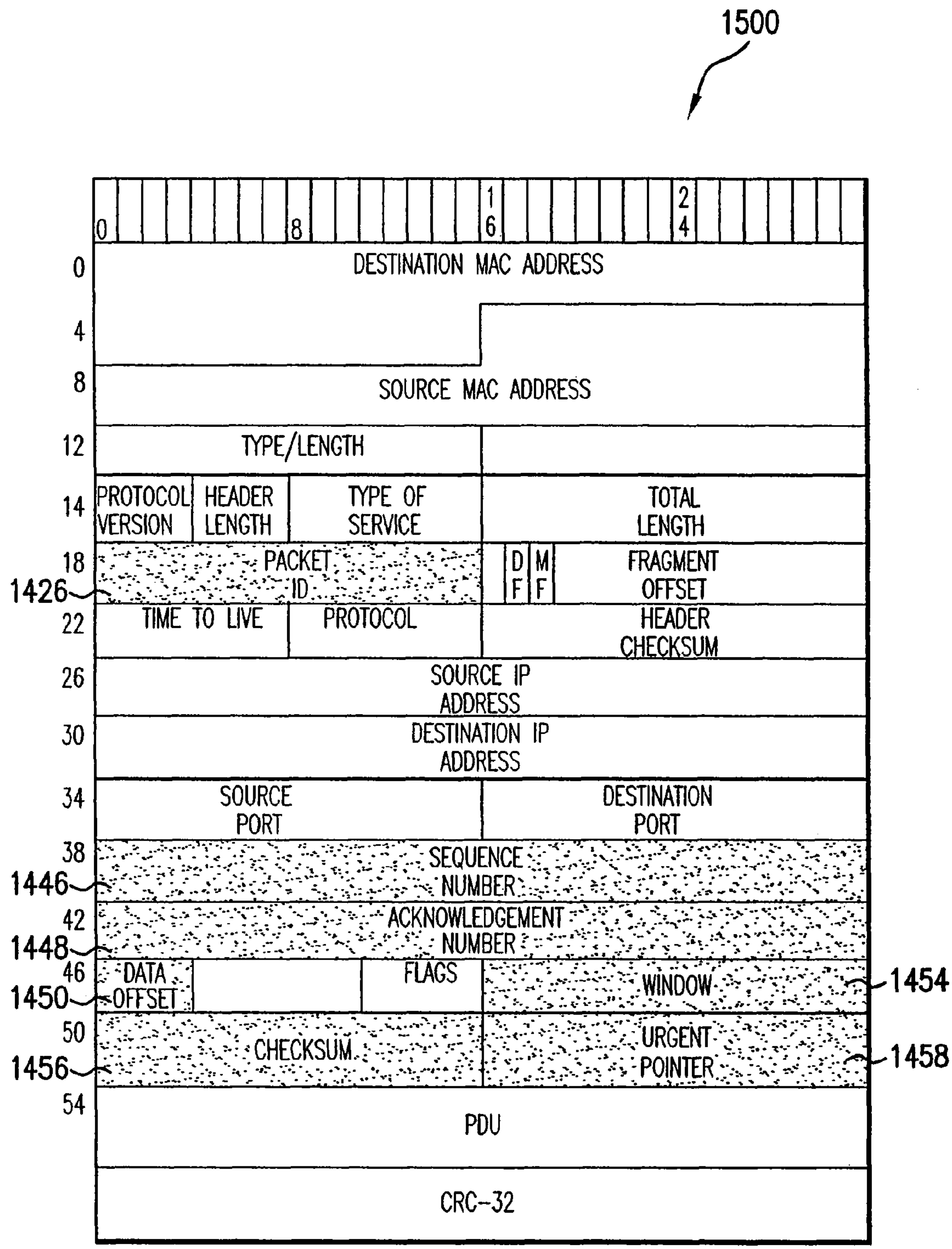
FIG. 15 is a diagram illustrating a TCP Protocol packet highlighting fields that may change from packet to packet.

FIG. 15 is a diagram illustrating the fields that change from packet to packet in TCP protocol packet 1410. The fields that change from packet to packet are highlighted. The changing fields include packet ID field 1426 from IP header 1404, and sequence number field 1446, acknowledgement number field 1448, data offset field 1450, window field 1454, checksum field 1456, and urgent pointer field 1458 from TCP header 1406.

Figure 16A:
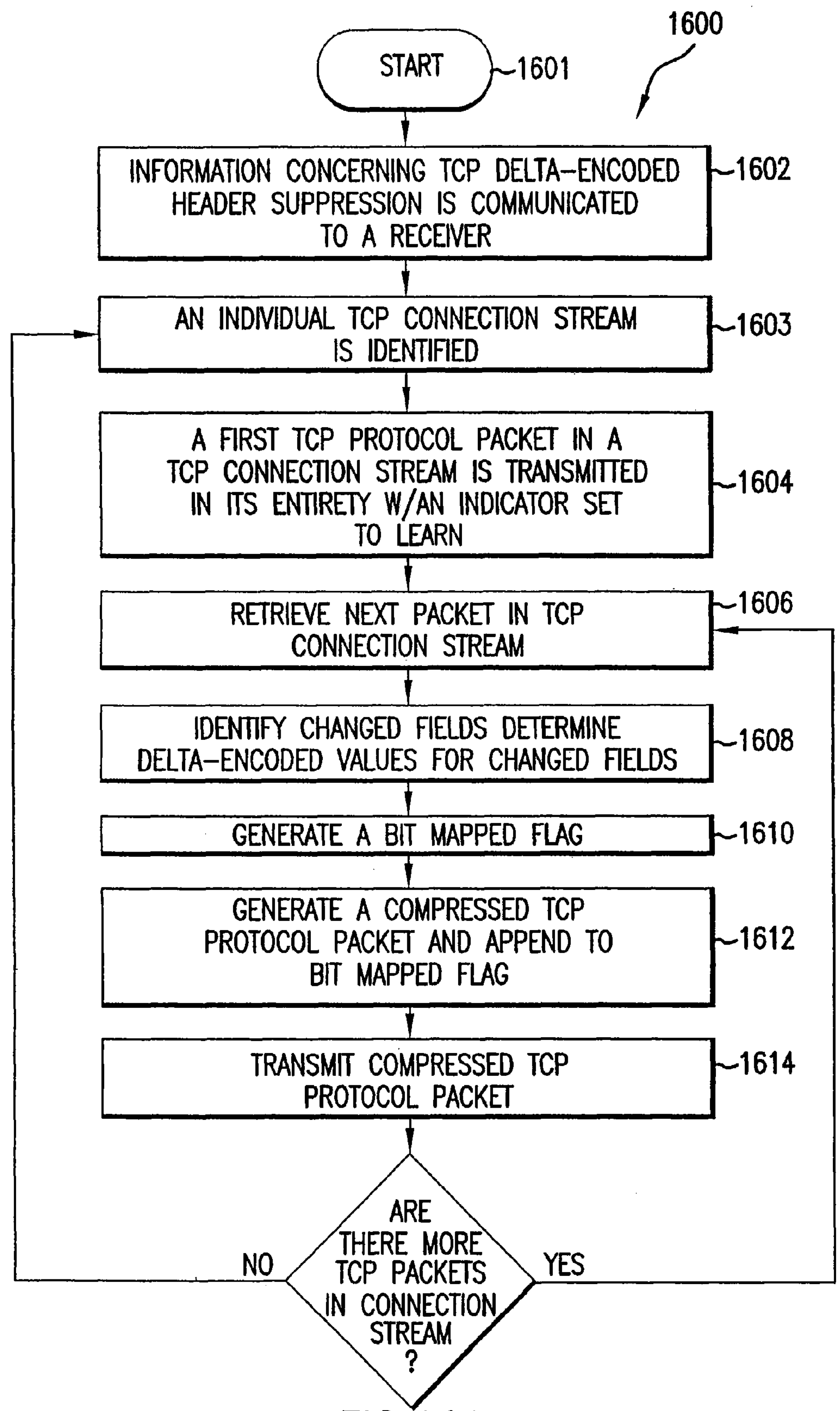
FIG. 16A is a high level diagram illustrating a method for a delta encoded header suppression technique according to an embodiment of the present invention.
Figure 16B:
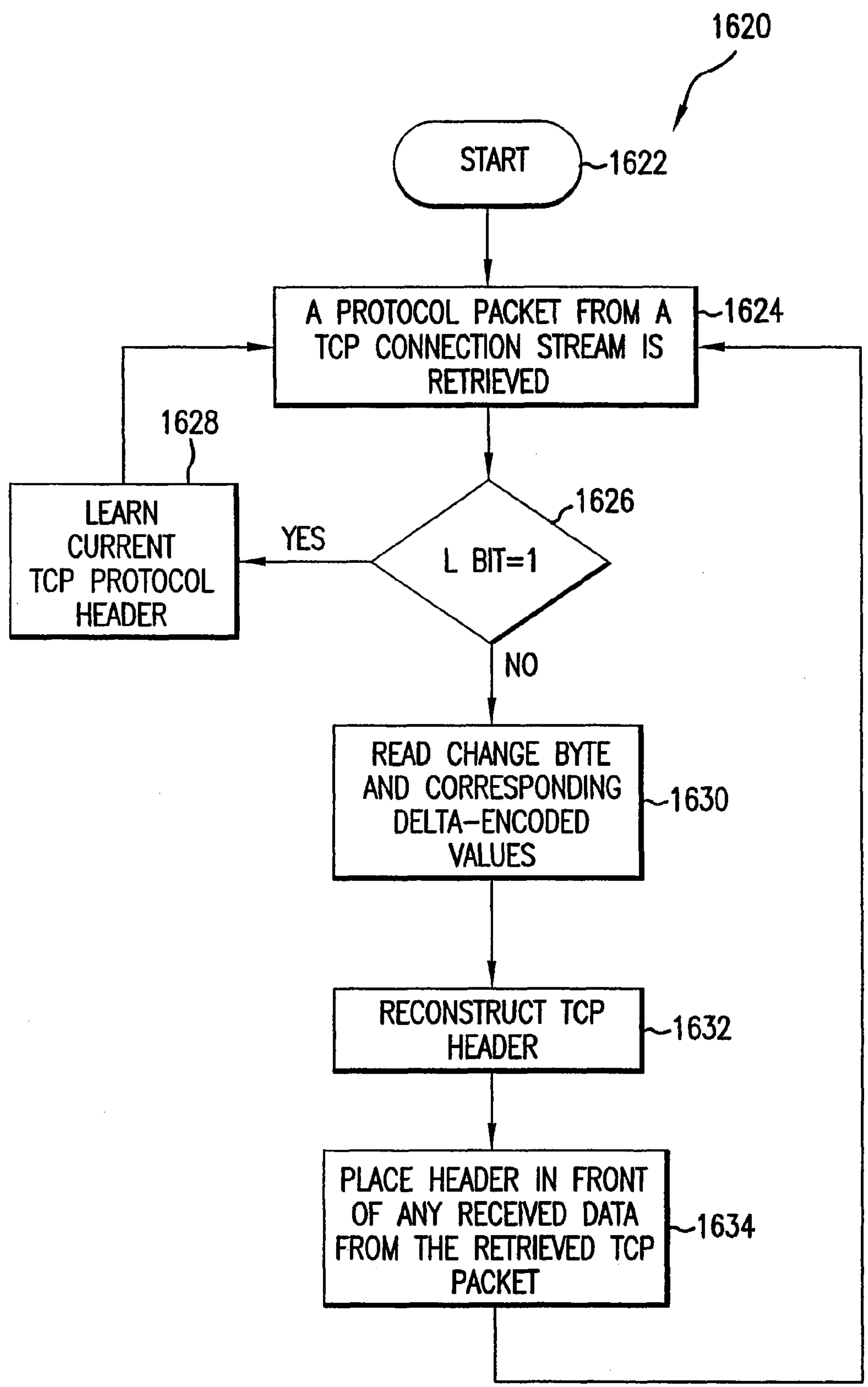
FIG. 16B is a high level diagram illustrating a method for a delta encoded header reconstruction technique according to an embodiment of the present invention.

The invention enables the in-order delivery of packets on the upstream DOCSIS RF link. The invention suppresses 802.3/IP/TCP header 1400 on CM 108 and ensures that header 1400 is reconstructed to its original format by CMTS 104. FIGS. 16A and 16B provide a high level description of the delta-encoded suppression and reconstruction process, respectively, for the present invention.

FIG. 16A is a high level flow diagram 1600 illustrating a method for a delta encoding suppression technique. The invention is not limited to the description provided herein with respect to flow diagram 1600. Rather, it will be apparent to persons skilled in the relevant art(s) after reading the teachings provided herein that other functional flow diagrams are within the scope of the present invention. The process begins with step 1601, and immediately proceeds to step 1602.

In step 1602, information concerning TCP delta-encoded header suppression is communicated from CM 108 to CMTS 104 to enable reconstruction of TCP packets at CMTS 104. As previously discussed, this may include an index number indicating the particular type of packet header suppression technique, the rules associated with suppressing and reconstructing a packet in accordance with the particular type of packet header suppression technique, etc. CM 108 chooses the suppression index, and thus, the suppression technique. This prevents the need for a two-way command transaction during fast data transfers. The process then proceeds to step 1603.

In step 1603, an individual TCP connection stream is identified. A framing protocol is used to separate and identify each TCP connection stream on a single DOCSIS SID. After identifying the TCP connection stream, the process proceeds to step 1604.

In step 1604, a first TCP protocol packet 1410 in a TCP connection stream is transmitted to a receiver in its entirety. The first TCP protocol packet 1410 includes a learn indicator. The indicator instructs the receiver to learn the complete header. The complete protocol header 1400 may be learned without requiring confirmation from a receiver, such as CMTS 104. This allows headers to be learned in real-time. Once the header has been learned, subsequent packets may be sent in a compressed format. Maximum efficiency is achieved by permitting an unsuppressed (learned) header to be immediately followed by a suppressed header. This eliminates the delay introduced in the DOCSIS approach which requires waiting for a learned acknowledgment from the receiver. The process then proceeds to step 1606.

In step 1606, the next packet in the TCP connection stream is retrieved. The process then proceeds to step 1608.

In step 1608, the fields that have changed from the previous transmitted packet are identified and a delta encoded value representing that change is determined. The process then proceeds to step 1610.

In step 1610, a bit-mapped flag is generated. The bit-mapped flag indicates which of the possible delta encoded IP/TCP field values are present between a change byte and the compressed TCP protocol packet's data area. The change byte is a one-byte bitmapped flag field for indicating which fields within protocol header 1400 have changed. The change byte will be discussed in more detail below with reference to FIG. 17. The process then proceeds to step 1612.

In step 1612, the compressed TCP protocol packet is generated and the bit-mapped flag is appended to the front of the compressed TCP packet. The process then proceeds to step 1614.

In step 1614, the compressed TCP protocol packet is transmitted to the receiver. The process then proceeds to decision step 1616.

In decision step 1616, it is determined whether there are more TCP protocol packets 1410 in the TCP connection stream to be transmitted. If there are more packets to be transmitted, then the process returns to step 1606 to retrieve the next packet.

Returning to decision step 1616, if there are no more packets to be transmitted in the TCP connection stream, the process will proceed back to step 1603, where another TCP connection stream is identified.

FIG. 16B is a high level flow diagram 1620 illustrating a method for a delta encoded header reconstruction technique. The invention is not limited to the description provided herein with respect to flow diagram 1620. Rather, it will be apparent to persons skilled in the relevant art(s) after reading the teachings provided herein that other functional flow diagrams are within the scope of the present invention. The process begins with step 1622, where the process immediately proceeds to step 1624.

In step 1624, a TCP protocol packet 1410 from a TCP connection stream is retrieved. The process then proceeds to decision step 1626.

In decision step 1626, it is determined whether the retrieved TCP protocol packet 1410 is to be learned. This is accomplished by determining whether the indicator learn bit is set. If the indicator learn bit is set, the process proceeds to step 1628.

In step 1628, the receiver learns the current TCP protocol header of packet 1410, and stores packet 1410 for future reference as a header template. The process then returns to step 1624 to retrieve another packet.

Returning to decision step 1626, if the indicator learn bit is not set, the process proceeds to step 1630.

In step 1630, the change byte is read and the corresponding delta-encoded values are read. The process then proceeds to step 1632.

In step 1632, the header is reconstructed. The TCP/IP header flags are updated and the delta-encoded values are used to update the changed fields in a stored header template. The process then proceeds to step 1634.

In step 1634, the completely restored header is placed in front of any received data from the TCP protocol packet retrieved in step 1624. At this point, the packet is completely restored to its original format, and can be transmitted over an IP network. The process then proceeds back to step 1624, where another TCP protocol packet is retrieved.

Figure 17:
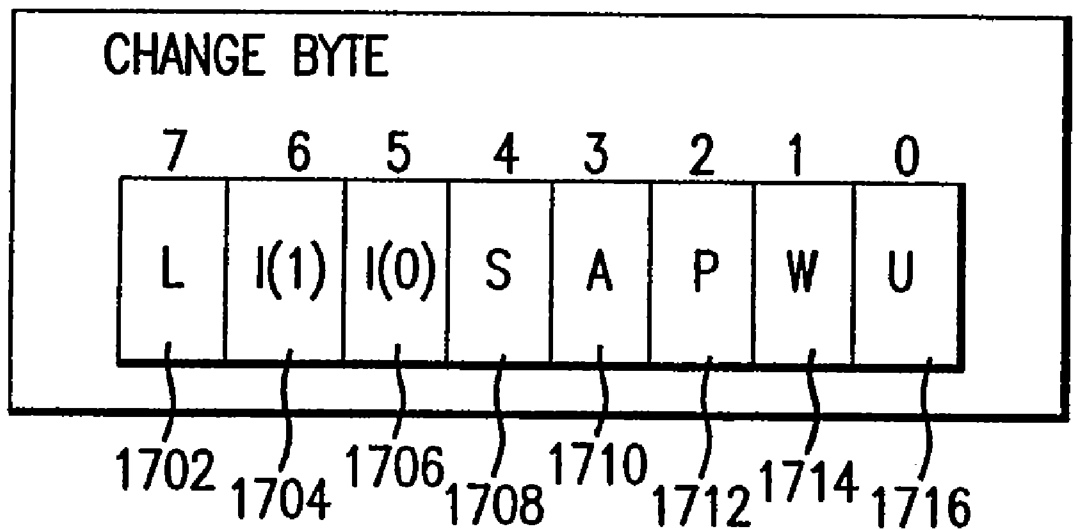
FIG. 17 is a diagram illustrating a change byte according to an embodiment of the present invention.

FIG. 17 is a diagram illustrating the change byte 1700 that is used in executing the delta-encoded header suppression technique. Change byte 1700 is a 1-byte bitmapped flag field for indicating which fields of protocol header 1400 have changed. Change byte 1700 also indicates whether or not header 1400 is to be learned at the receiving end. Change byte 1700 further indicates whether to increment IP packet ID 1426 and the amount by which EP packet ID 1426 should be incremented. Change byte 1700 comprises an L bit 1702, an I(1) bit 1704, an I(0) bit 1706, an S bit 1708, an A bit 1710, a P bit 1712, a W bit 1714, and a U bit 1716.

L bit 1702, when set, indicates that the remainder of the change byte can be ignored and that an entire 54-byte 802.3/IP/TCP header 1400 is included in the burst and should be used to replace the current template header.

I(1) bit 1704 and I(0) bit 1706 are used to determine the change for IP packet ID field 1426 in a similar manner as indicated in Table 1 above. I(1) bit 1704, when set, indicates that the next value in the data stream is a 2-byte value to be copied to IP packet ID field 1426 of the template header. The result should be written back to the template header and emitted. When I(1) bit 1704 is clear, I(0) bit 1706, must be checked to determine how to increment IP packet ID 1426. I(0) bit 1706, when set, indicates that 0x0100 should be added to the template header IP packet ID field 1426, written back to the template header, and emitted. When clear, I(0) bit 1706 indicates that the template header IP packet ID field 1426 should be incremented by 0x0001, written back to the template header, and emitted. I(1) bit 1704 and I(0) bit 1706 are determined based upon the operation of modern IP protocol stacks and the manner in which they are incremented as described above.

S bit 1708, when set, indicates that the next value in the data stream is a 2-byte value to be added to the 4-byte TCP sequence number field 1446 of the template header. The result should be written back to the template header and emitted. When S bit 1708 is clear, TCP sequence number field 1446 of the template header should be used as is.

When A bit 1710 is set, the next value in the data stream is a 2-byte value to be added to the 4-byte TCP acknowledgement number field 1448 of the template header. The result should be written back to the template header and emitted. When A bit 1710 is clear, TCP acknowledgement number field 1448 of the template header should be used as is.

P bit 1712, when set, indicates that the PUSH bit (not shown) of a nibble of TCP flags field 1452 should be set and emitted. When P bit 1712 is clear, the PUSH bit of a nibble of TCP flags field 1452 should be cleared and emitted.

When W bit 1714 is set, the next value in the data stream is a 2-byte value to be copied to TCP window field 1454 of the template header. The result should be written back to the template header and emitted. When W bit 1714 is clear, TCP window field 1454 of the template header should be used as is.

When U bit 1716 is set, the next value in the data stream is a 2-byte value to be copied to TCP urgent pointer field 1458 of the template header. The result should be written back to the template header and emitted. When U bit 1716 is clear, TCP urgent pointer field 1458 of the template header should be used as is.

Based on the fields that actually change from the previous transmitted values, one of two actions will occur. TCP protocol packet 1410 may be sent without any suppression whatsoever or TCP protocol packet 1410 may be appended to change byte 1700 and include either an entire TCP protocol packet 1410 or two or more fields in place of 54-byte 802.3/IP/TCP header 1400. The two or more fields that replace 802.3/IP/TCP header 1400 include: (1) an actual IP packet ID 1426 value (which is sent only if IP packet ID did not increment by 0x0001 or 0x0100); (2) a delta-encoded value for TCP sequence number 1446 (which is sent only if the delta-encoded TCP sequence number ≠ 0); (3) a delta-encoded value for TCP acknowledgement number field 1448 (which is sent only if the delta-encoded TCP acknowledgement number ≠ 0); (4) a byte of data for TCP data offset field 1450; (5) an actual value for TCP window field 1454 (which is sent only if a delta value for TCP window field 1454 ≠ 0); (6) an actual value for TCP header checksum field 1456; and (7) an actual value for TCP urgent pointer field 1458 (which is sent only if IP urgent flag is set). The invention, therefore, uses a framing mechanism that combines compressed, uncompressed, and non-IP style traffic on a single DOCSIS SID.

Traditional Internet TCP/IP header suppression protocols use a variable length delta encoding scheme to represent changing fields. The present technique is optimized for characteristics of high-speed TCP/IP networks. For such networks, the changing TCP fields (i.e., ACK, SEQ, WIN) typically increment by more than 255 units. Encoding these changes with a fixed, two-byte delta field optimizes the typical case for high-speed networks, and reduces the processing required for each transmitted TCP protocol packet 1410.

Figure 18:
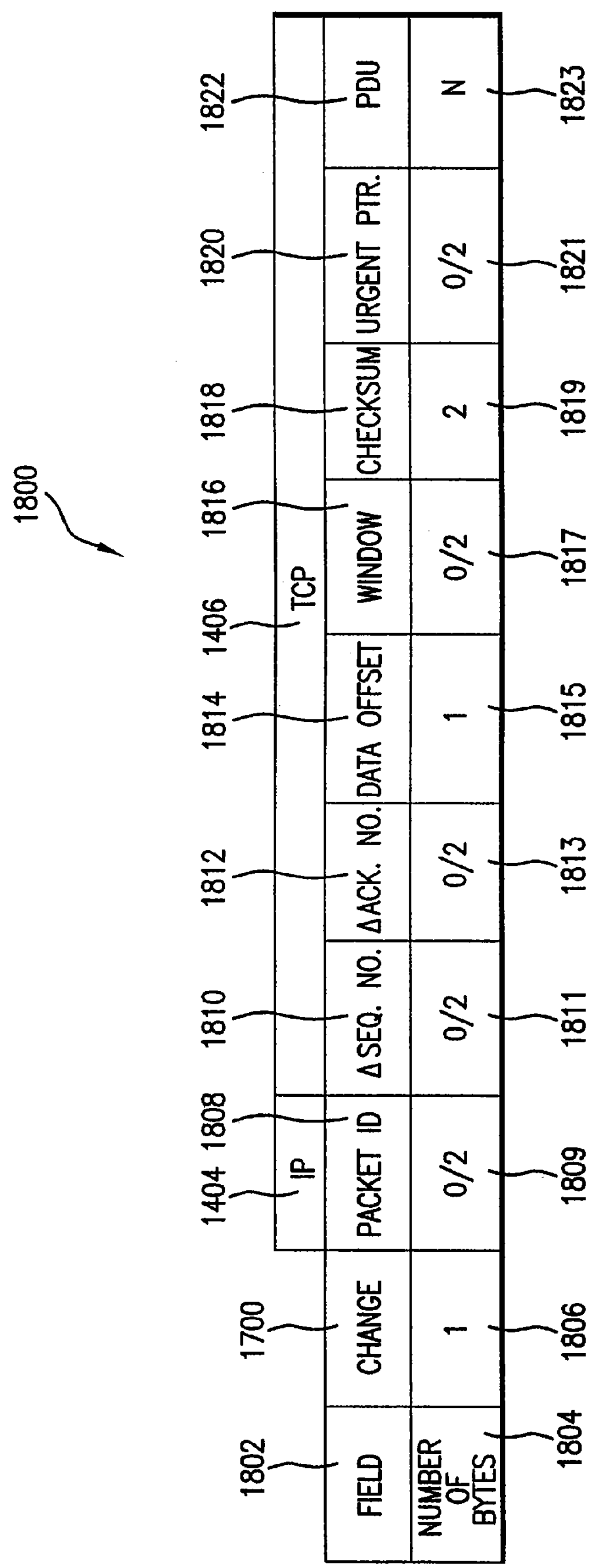
FIG. 18 is a diagram illustrating a final encoded data stream according to an embodiment of the present invention.

FIG. 18 is a diagram illustrating a final encoded data stream 1800 that is sent to a receiver (i.e., CMTS) when L bit 1702 is not set. FIG. 18 shows a first row 1802 for each field in final encoded data stream 1800 and a second row 1804 indicating a number of bytes that correspond to each field in final encoded data stream 1800.

A first field 1806 is change byte 1700. As previously indicated, change byte 1700 is comprised of 1-byte 1806.

A second field 1808 is a delta-encoded value for IP packet ID field 1426. Delta-encoded value 1808 for IP packet ID field 1426 may consist of either 0 or 2-bytes of data (1809), depending upon whether a value is to be copied into the template header for IP packet ID field 1426 or if the value of EP packet ID field 1426 is to be incremented by either 0x0001 or 0x0100. If a value is to be copied into the template header for IP packet ID field 1426, then final encoded data stream 1800 will contain 2-bytes for IP packet ID field 1426. If a value is not to be copied into the template header for IP packet ID field 1426, then final encoded data stream 1800 will not contain any bytes for IP packet ID 1426. Instead, an increment value for IP packet ID field 1426 will be determined using bits I(1) 1704 and I(0) 1706 of change byte 1700.

A third field 1810 is a delta-encoded value for TCP sequence number 1446. Delta-encoded value 1810 for TCP sequence number field 1446 may consist of either 0 or 2-bytes of data (1811), depending upon whether a change occurred in TCP sequence number field 1446 from the previous transmitted value. If a change occurred in TCP sequence number 1446 from the previous transmitted value, S bit 1708 of change byte 1700 will be set and final encoded data stream 1800 will contain 2-bytes of data for updating TCP sequence number field 1446 in the template header. If a change did not occur in TCP sequence number field 1446 from the previous transmitted value, S bit 1708 of change byte 1700 will not be set and final encoded data stream 1800 will not contain any bytes for TCP sequence number field 1446.

A fourth field 1812 is a delta-encoded value for TCP acknowledgement number field 1448. Delta-encoded value 1812 for TCP acknowledgement number field 1448 may consist of either 0 or 2-bytes of data (1813), depending upon whether a change occurred in TCP acknowledgement number field 1448 from the previous transmitted value. If a change occurred in TCP acknowledgement number field 1448 from the previous transmitted value, A bit 1710 of change byte 1700 will be set and final encoded data stream 1800 will contain 2-bytes of data for updating TCP acknowledgement number field 1448 in the template header. If a change did not occur in sequence number field 1446 from the previous transmitted value, A bit 1710 of change byte 1700 will not be set and final encoded data stream 1800 will not contain any bytes for TCP acknowledgement number field 1448.

A fifth field 1814 is for TCP data offset field 1450. A value for TCP data offset field 1450 consists of 1-byte of data (1815) to be inserted in final encoded data stream 1800.

A sixth field 1816 is for TCP window field 1454. A value for TCP window field 1454 may consist of 0 or 2-bytes of data (1817), depending upon whether a change occurred in TCP window field 1454 from the previous transmitted value. If a change occurred in TCP window field 1454 from the previous transmitted value, W bit 1714 of change byte 1700 will be set and final encoded data stream 1800 will contain 2-bytes of data for updating TCP window field 1454 in the template header. If a change did not occur in TCP window field 1454 from the previous transmitted value, W bit 1714 of change byte 1700 will not be set and final encoded data stream 1800 will not contain any bytes for TCP window field 1454.

A seventh field 1818 is for TCP checksum field 1456. A value for TCP checksum field 1456 consists of 2-bytes of data (1819) to be inserted in final encoded data stream 1800.

An eighth field 1820 is for TCP urgent pointer field 1458. A value for TCP urgent pointer field 1458 may consist of 0 or 2-bytes of data (1821), depending upon whether an IP urgent flag in TCP flags field 1452 is set. If the IP urgent flag in TCP flags field 1452 is set, U bit 1716 of change byte 1700 will be set and final encoded data stream 1800 will contain 2-bytes of data to be copied into the template header. If the IP urgent flag in TCP flags field 1452 is not set, U bit 1716 of change byte 1700 will not be set and final encoded data stream 1800 will not contain any bytes for TCP urgent pointer field 1458.

A ninth field 1822 is for TCP PDU 1460. TCP PDU may consist of 0-n bytes (1823).

Figure 19:
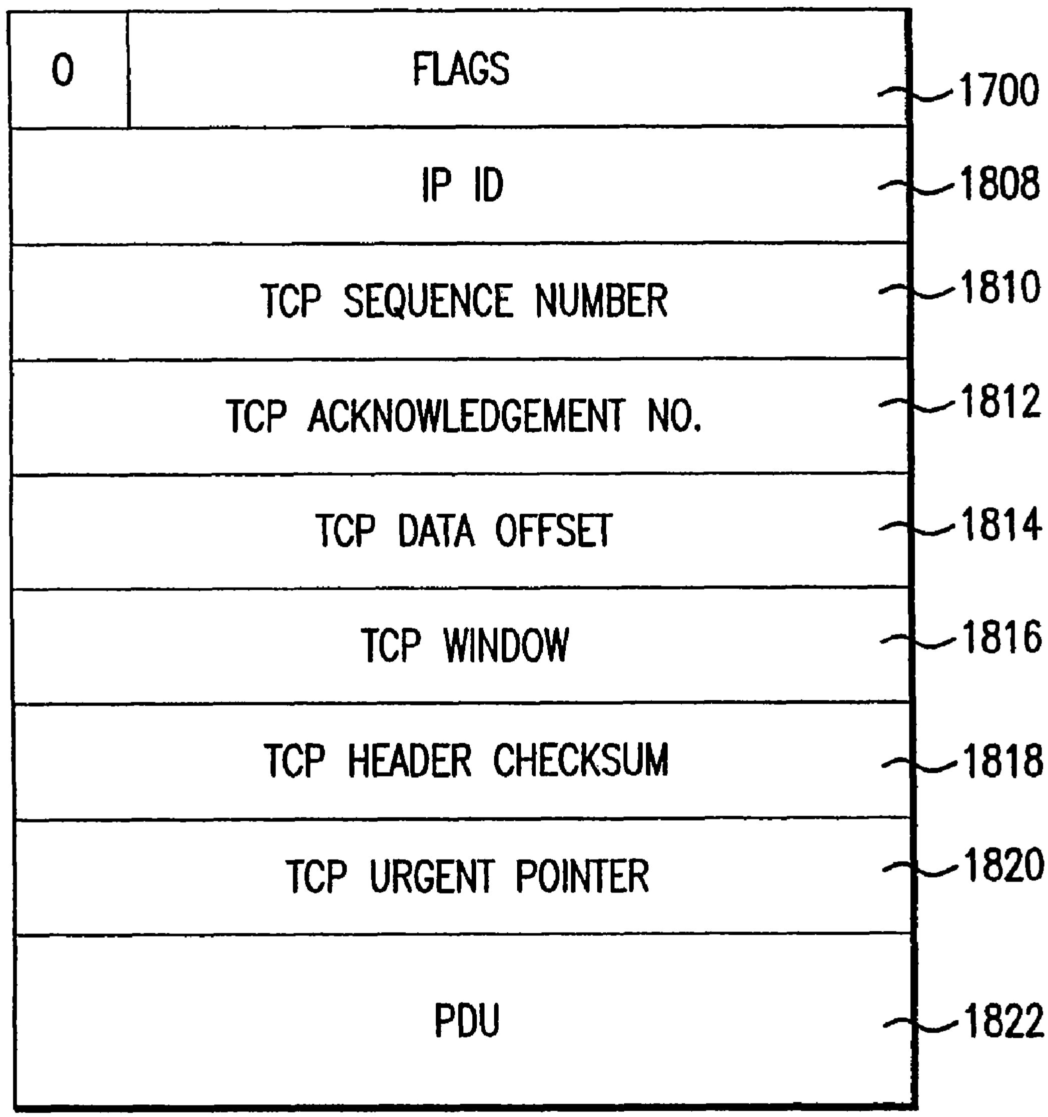
FIG. 19 is a diagram illustrating the transmit order of data for TCP header suppression for a non-learning state according to an embodiment of the present invention.

FIG. 19 is a diagram illustrating a transmit order 1900 for final encoded data stream 1800 when L bit 1702 is not set. Transmit order 1900 begins with change byte 1700. Fields 1808, 1810, 1812, 1814, 1816, 1818, 1820, and 1822 follow.

Figure 20:
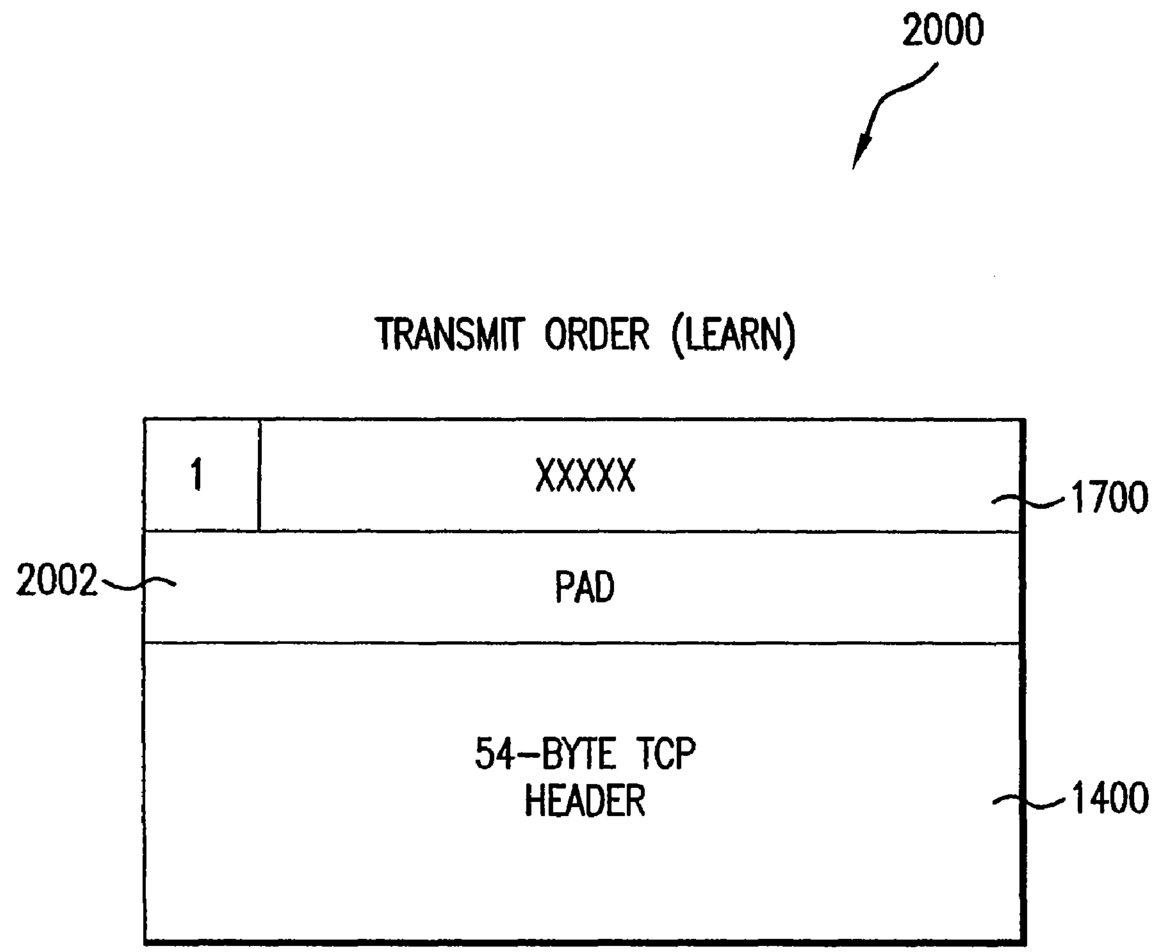
FIG. 20 is a diagram illustrating the transmit order of data for TCP header suppression for a learn state according to an embodiment of the present invention.

FIG. 20 is a diagram illustrating a transmit order 2000 when L bit 1702 is set. This indicates that the header information being transmitted is to be learned by the receiver. Transmit order 2000 consists of change byte 1700, a pad 2002, 54-byte TCP protocol header 1410, and PDU 1460.

Figure 21:
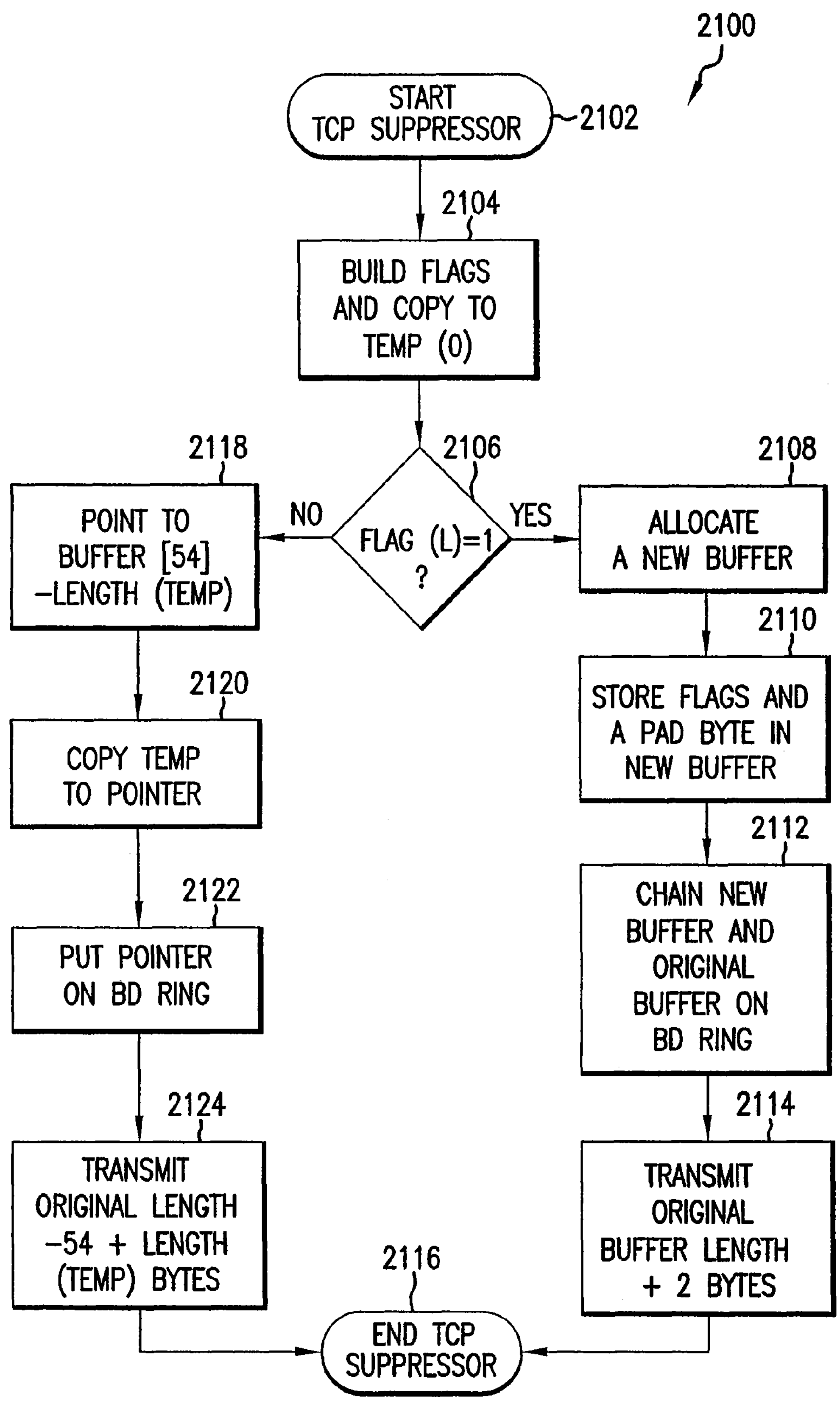
FIG. 21 is a flow diagram illustrating a method for TCP header suppression according to an embodiment of the present invention.

FIG. 21 is a flow diagram 2100 illustrating a method for TCP header suppression. The invention is not limited to the description provided herein with respect to flow diagram 2100. Rather, it will be apparent to persons skilled in the relevant art(s) after reading the teachings provided herein that other functional flow diagrams are within the scope of the present invention. The process begins with step 2102, where a TCP suppressor is started. The process then proceeds to step 2104.

In step 2104, L bit 1702, I(1) bit 1704, I(0) bit 1706, S bit 1708, A bit 1710, P bit 1712, W bit 1714, and U bit 1716 of change byte 1700 are determined. The change byte is then copied to temp(0). The process then proceeds to decision step 2106.

In decision step 2106, it is determined whether L bit 1702 is set. If L bit 1702 is set, this indicates that 802.3/IP/TCP should be sent in its entirety to be learned by a receiver, such as CMTS 104. The process then proceeds to step 2108.

In step 2108, a new buffer is allocated. The process then proceeds to step 2110.

In step 2110, change byte 1700 and a single pad byte are stored in the buffer allocated in step 2108. The system hardware does not like to see buffers with an allocation of a single byte. Thus a hardware constraint is to provide buffers with more than 1-byte. Thus, a pad byte is also inserted into the buffer. The process then proceeds to step 2112.

In step 2112, an original buffer which holds TCP protocol packet 1410 is appended to the new buffer on a BD ring. The process then proceeds to step 2114.

In step 2114, the original buffer length and the new buffer length are transmitted. Thus, the change byte and a pad are transmitted with the 54-byte header and PDU 1460 for learning the complete 802.3/IP/TCP header 1400. When L bit 1702 is set, transmit order 2000 applies. The process then proceeds to step 2116, where the process ends.

Returning to decision step 2106, if L bit 1702 is not set, the process then proceeds to step 2118. In step 2118, the length of temp is calculated, and a pointer is set to buffer [54] minus the length of temp. The length of temp includes the length of all of the data being sent in final encoded data stream 1800. The process then proceeds to step 2120.

In step 2120, temp is copied to the pointer. The process then proceeds to step 2122.

In step 2122, the pointer is put on the BD ring. The process then proceeds to step 2124.

In step 2124, the original length −[54]+length of temp is transmitted. Thus, final encoded data stream 1800 is transmitted. When L bit 1702 is not set, transmit order 1900 applies. The process then proceeds to step 2116, where the process ends.

Figure 22A:
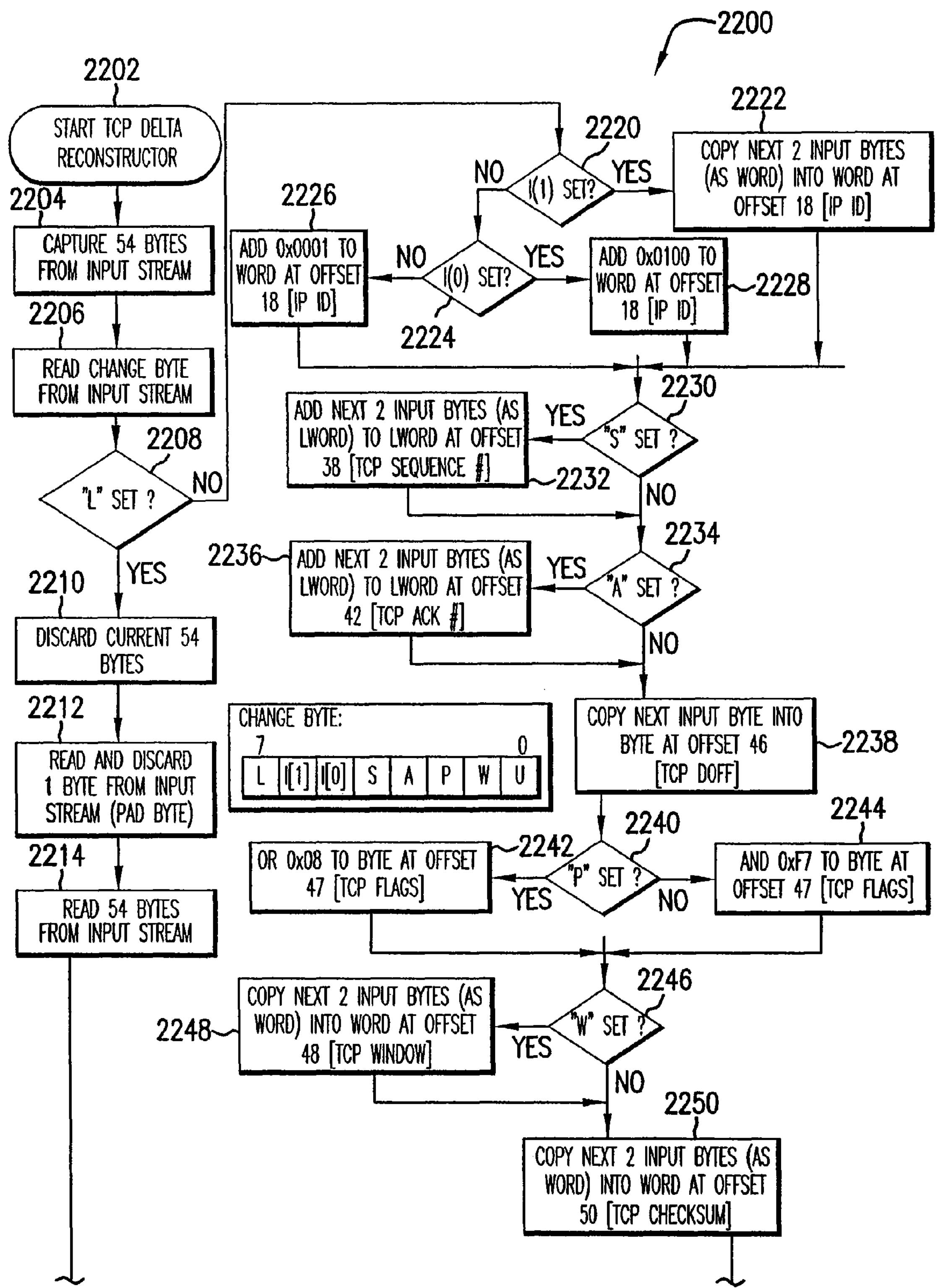
FIG. 22 is a flow diagram illustrating a method for TCP header reconstruction according to an embodiment of the present invention.
Figure 22B:
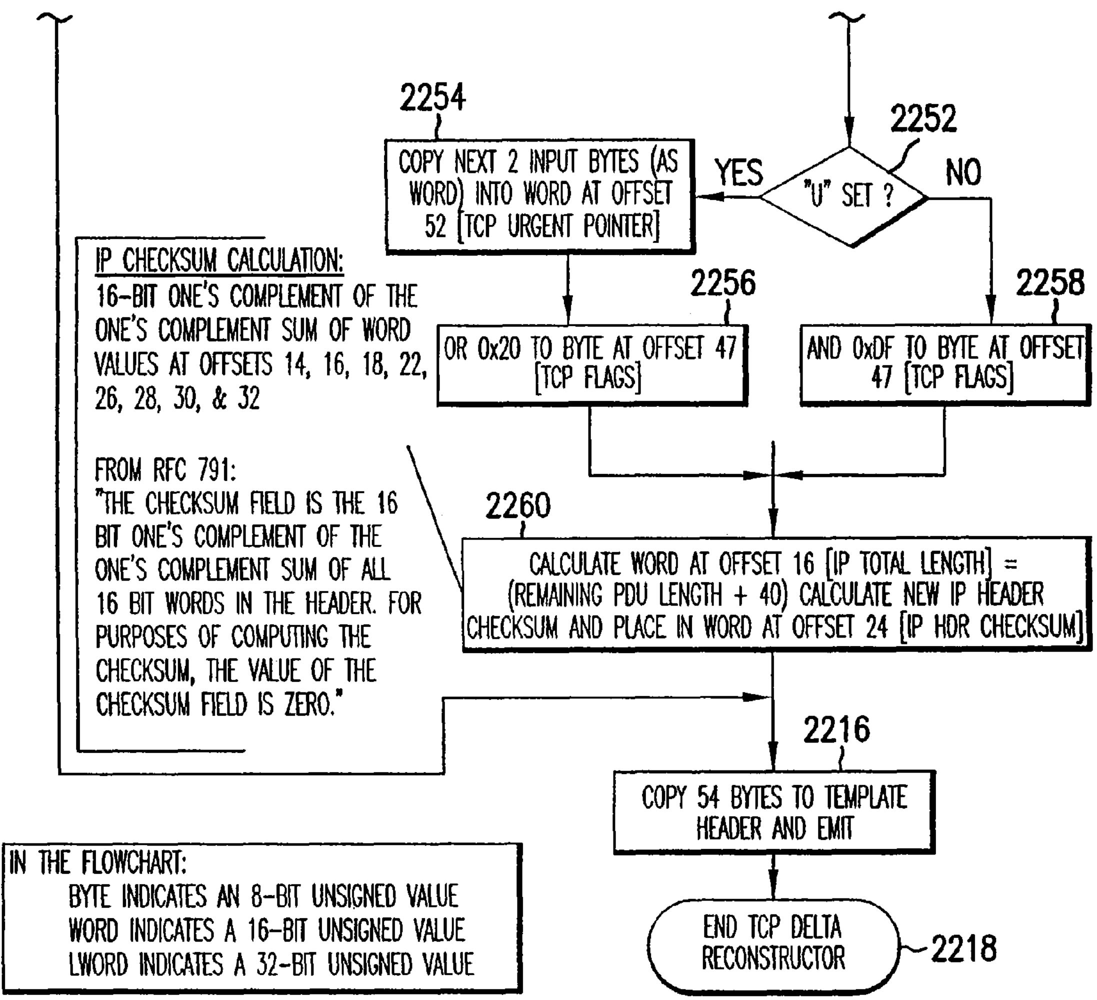

FIG. 22 is a flow diagram 2200 illustrating a method for TCP header reconstruction. The invention is not limited to the description provided herein with respect to flow diagram 2200. Rather, it will be apparent to persons skilled in the relevant art(s) after reading the teachings provided herein that other functional flow diagrams are within the scope of the present invention. A 54-byte template header is generated by the DOCSIS payload header reconstruction engine (not shown) prior to the start of flow diagram 2200. The process begins with step 2202, where a TCP header reconstructor is started. The process then proceeds to step 2204.

In step 2204, a 54-byte header is read from the input stream. The process then proceeds to step 2206.

In step 2206, change byte 1700 is read from the input stream. The process then proceeds to decision step 2208.

In decision step 2208, it is determined whether L bit 1702 from change byte 1700 is set. If L bit 1702 is set, then the process proceeds to step 2210.

In step 2210, the 54-byte header that was captured in step 2204 is discarded. This data is discarded because this data was not generated from the input stream, but was generated from the hardware's payload header suppression mechanism at the end of the reconstructor process, which will be discussed below with reference to step 2216. When the hardware's payload header suppression mechanism injects this 54-byte header, the 54-byte header is placed prior to change byte 1700. Thus, when L bit 1702 is set, this 54-byte header is considered garbage and must be discarded. From the point of view of CM 108, what was sent was a suppression index. Receipt of the suppression index by CMTS 104 caused CMTS 104 to inject 54-bytes of incorrect data into the data stream. The process then proceeds to step 2212.

In step 2212, a 1-byte pad is read from the input stream and discarded. The process then proceeds to step 2214.

In step 2214, the correct 54-byte header, transmitted from CM 108, is read from the input stream. The process then proceeds to step 2216.

In step 2216, the correct 54-byte header is copied to a template header and the 54-byte header and the data from PDU 1460 that follows is emitted. The process then proceeds to step 2218, where the process ends.

Returning to decision step 2208, if L bit 1702 of change byte 1700 is not set, then the process proceeds to decision step 2220.

Decision step 2220 begins the process for determining whether to increment IP packet ID field 1426 by 0x0001 or 0x0100 or to copy a 2-byte value from the input stream into the template header of IP packet ID field 1426. In decision step 2220, it is determined whether I(1) bit 1704 of change byte 1700 is set. If I(1) is set, the process proceeds to step 2222.

In step 2222, a 2-byte value is read from the input stream and copied into IP packet ID field 1426 (offset 18). The process then proceeds to step 2230.

Returning to decision step 2220, if I(1) bit 1704 of change byte 1700 is not set, the process proceeds to decision step 2224. In decision step 2224, it is determined whether I(0) bit 1706 of change byte 1700 is set. If I(0) bit 1706 is not set, the process proceeds to step 2226.

In step 2226, 0x0001 is added to IP packet ID 1426 at offset 18. The process then proceeds to step 2230.

Returning to decision step 2224, if I(0) bit 1706 of change byte 1700 is set, the process proceeds to step 2228. In step 2228, 0x0100 is added to IP packet ID 1426 at offset 18. The process then proceeds to decision step 2230.

In decision step 2230, it is determined whether S bit 1708 of change byte 1700 is set. If S bit 1708 is set, indicating that a change has occurred in TCP sequence number field 1446 from the previous value, the process proceeds to step 2232.

In step 2232, the next 2-bytes of data from the input data stream are added to TCP sequence number field 1446 at offset 38. The process then proceeds to decision step 2234.

Returning to decision step 2230, if S bit 1708 of change byte 1700 is not set, the process proceeds to decision step 2234.

In decision step 2234, it is determined whether A bit 1710 of change byte 1700 is set. If A bit 1710 is set, indicating that a change has occurred in TCP acknowledgement number field 1448, then the process proceeds to step 2236.

In step 2236, the next 2-bytes of data from the input stream are added to TCP acknowledgement number field 1448 at offset 42. The process then proceeds to step 2238.

Returning to decision step 2234, if A bit 1710 of change byte 1700 is not set, then the process proceeds to step 2238.

In step 2238, the next byte of data from the input stream is copied into TCP data offset field 1450 at offset 46. The process proceeds to decision step 2240.

In decision step 2240, it is determined whether P bit 1712 of change byte 1700 is set. If P bit 1712 is set, the process proceeds to step 2242.

In step 2242, 0x08 is ORed with the data in TCP flag field 1452 at offset 47. The process proceeds to decision step 2246.

Returning to decision step 2240, if P bit 1712 of change byte 1700 is not set, the process proceeds to step 2244.

In step 2244, 0xF7 is ANDed with the data in TCP flag field 1452 at offset 47. The process proceeds to decision step 2246.

In decision step 2246, it is determined whether W bit 1714 of change byte 1700 is set. If W bit 1714 is set, indicating that a change has occurred in TCP window field 1454, the process proceeds to step 2248.

In step 2248, the next 2-bytes of data from the input stream are copied into TCP window field 1454 at offset 48. The process then proceeds to step 2250.

Returning to decision step 2246, if it is determined that W bit 1714 of change byte 1700 is not set, the process proceeds to step 2250.

In step 2250, the next 2-bytes of data from the input stream are copied into TCP checksum field 1456 at offset 50. The process then proceeds to decision step 2252.

In decision step 2252, it is determined whether U bit 1716 of change byte 1700 is set. If U bit 1716 is set, the process proceeds to step 2254.

In step 2254, the next 2-bytes of data from the input stream are copied into TCP urgent pointer field 1458 at offset 52. The process then proceeds to step 2256.

In step 2256, the U bit in TCP flags field 1452 is set by Oring 0x20 to TCP flags field 1452 at offset 47. The process then proceeds to step 2260.

Returning to decision step 2252, if U bit 1716 of change byte 1700 is not set, then the process proceeds to step 2258. In step 2258, the U bit in TCP flags field 1452 is cleared by ANDing 0xDF to TCP flags field 1452 at offset 47. The process then proceeds to step 2260.

In step 2260, IP total length field 1424 is set equal to the remaining PDU 1460 length plus 40 bytes. A new IP header checksum field 1434 is determined and placed in the template header at offset 24. IP header checksum is the 16-bit one's complement of the one's complement sum of the values at offsets 14, 16, 18, 22, 26, 28, 30, and 32. The process then proceeds to step 2216, where 54-bytes are copied to the template header and emitted. The process then proceeds to step 2218, where the process ends.

D. Environment

As discussed elsewhere herein, the above-described techniques or methods may be executed as software routines, in part, by the MAC portion of a cable modem and the headend MAC portion of a CMTS. For example, with reference to the example implementation of cable modem 108 described in reference to FIG. 3, MAC 314 performs necessary method steps by executing software functions with the assistance of CPU 320. These software functions may be stored in either RAM 322 or ROM 324. Furthermore, with reference to the example implementation of CMTS 104, headend MAC 218 performs necessary method steps by executing software functions with the assistance of CPU 222. These software functions may be stored in either RAM 220 or ROM 218.

Figure 23:
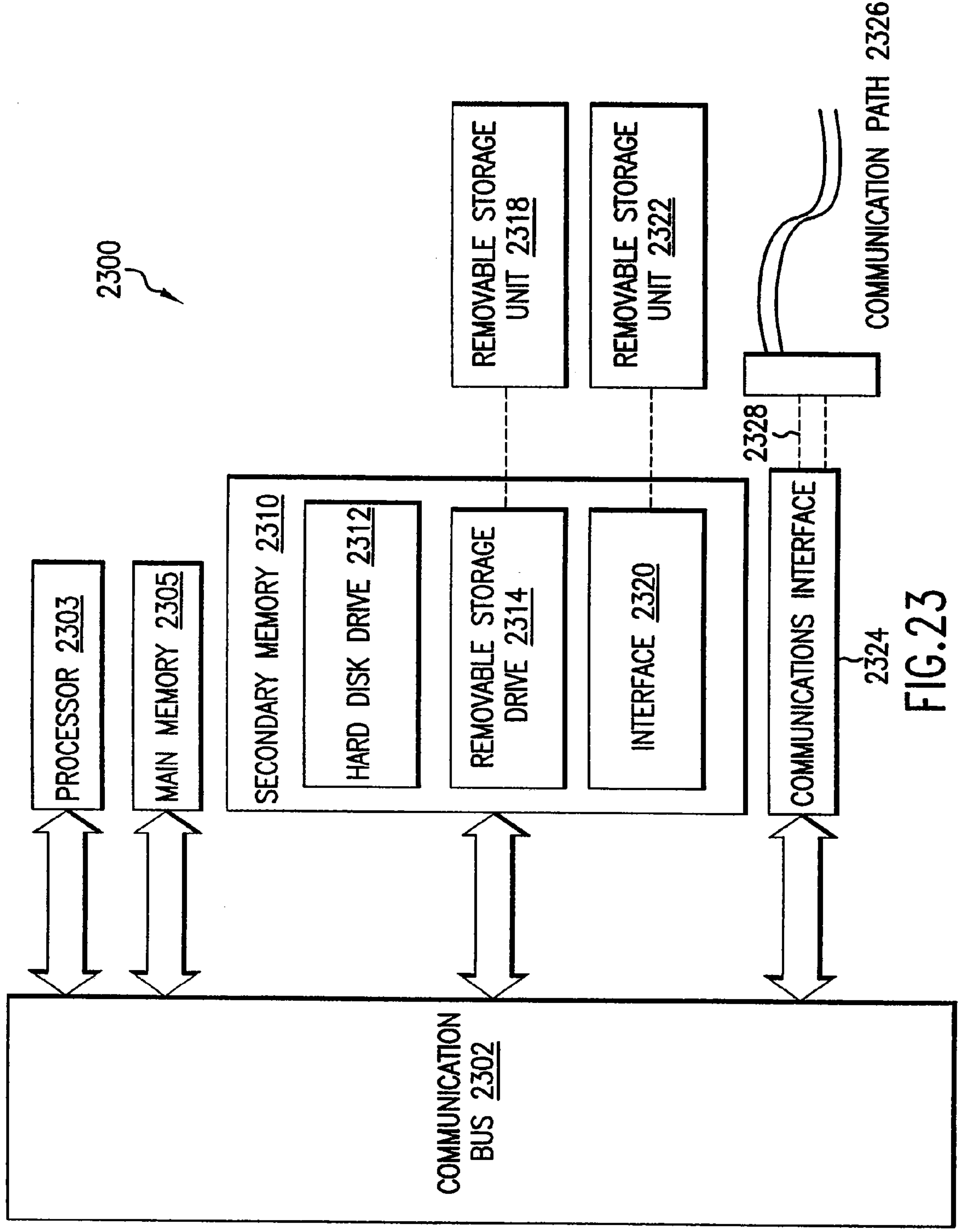
FIG. 23 is a diagram illustrating an exemplary computer system.

However, methods of the present invention need not be limited to these embodiments. For example, the methods of the present invention may be embodied in software routines which are executed on computer systems, such as a computer system 2300 as shown in FIG. 23. Various embodiments are described in terms of this exemplary computer system 2300. After reading this description, it will be apparent to a person skilled in the relevant art how to implement the invention using other computer systems and/or computer architectures. The computer system 2300 includes one or more processors, such as processor 2303. The processor 2303 is connected to a communication bus 2302.

Computer system 2300 also includes a main memory 2305, preferably random access memory (RAM), and may also include a secondary memory 2310. The secondary memory 2310 may include, for example, a hard disk drive 2312 and/or a removable storage drive 2314, representing a floppy disk drive, a magnetic tape drive, an optical disk drive, etc. The removable storage drive 2314 reads from and/or writes to a removable storage unit 2318 in a well-known manner. Removable storage unit 2318, represents a floppy disk, magnetic tape, optical disk, etc., which is read by and written to by removable storage drive 2314. As will be appreciated, the removable storage unit 2318 includes a computer usable storage medium having stored therein computer software and/or data.

In alternative embodiments, secondary memory 2310 may include other similar means for allowing computer programs or other instructions to be loaded into computer system 2300. Such means may include, for example, a removable storage unit 2322 and an interface 2320. Examples of such may include a program cartridge and cartridge interface (such as that found in video game devices), a removable memory chip (such as an EPROM, or PROM) and associated socket, and other removable storage units 2322 and interfaces 2320 which allow software and data to be transferred from the removable storage unit 2322 to computer system 2300.

Computer system 2300 may also include a communications interface 2324. Communications interface 2324 allows software and data to be transferred between computer system 2300 and external devices. Examples of communications interface 2324 may include a modem, a network interface (such as an Ethernet card), a communications port, a PCMCIA slot and card, a wireless LAN (local area network) interface, etc. Software and data transferred via communications interface 2324 are in the form of signals 2328 which may be electronic, electromagnetic, optical, or other signals capable of being received by communications interface 2324. These signals 2328 are provided to communications interface 2324 via a communications path (i.e., channel) 2326. This channel 2326 carries signals 2328 and may be implemented using wire or cable, fiber optics, a phone line, a cellular phone link, a wireless link, and other communications channels.

In this document, the term "computer program product" refers to removable storage units 2318, 2322, and signals 2328. These computer program products are means for providing software to computer system 2300. The invention is directed to such computer program products.

Computer programs (also called computer control logic) are stored in main memory 2305, and/or secondary memory 2310 and/or in computer program products. Computer programs may also be received via communications interface 2324. Such computer programs, when executed, enable the computer system 2300 to perform the features of the present invention as discussed herein. In particular, the computer programs, when executed, enable the processor 2303 to perform the features of the present invention. Accordingly, such computer programs represent controllers of the computer system 2300.

In an embodiment where the invention is implemented using software, the software may be stored in a computer program product and loaded into computer system 2300 using removable storage drive 2314, hard drive 2312 or communications interface 2324. The control logic (software), when executed by the processor 2303, causes the processor 2303 to perform the functions of the invention as described herein.

In another embodiment, the invention is implemented primarily in hardware using, for example, hardware components such as application specific integrated circuits (ASICs). Implementation of hardware state machine(s) so as to perform the functions described herein will be apparent to persons skilled in the relevant art(s).

In yet another embodiment, the invention is implemented using a combination of both hardware and software.

E. CONCLUSION

The present invention is not limited to the embodiment of a cable modem system. The present invention can be used with any system that transmits packets over a network. The previous description of the preferred embodiments is provided to enable any person skilled in the art to make or use the present invention. While the invention has been particularly shown and described with reference to preferred embodiments thereof, it will be understood by those skilled in the art that various changes in form and detail may be made therein without departing from the spirit and scope of the invention.

What is claimed is:

1. A subscriber station in a wireless communication system, comprising:

a media access control;

a wireless receiver coupled to the media access control; and a wireless transmitter coupled to the media access control;

wherein the media access control is configured to generate a registration message that indicates support for a plurality of protocol-specific header suppression techniques by the subscriber station and wherein the wireless transmitter is configured to wirelessly transmit the registration message to a base station;

wherein the wireless receiver is configured to wirelessly receive a response to the registration message from the base station and to provide the response to the registration message to the media access control, the response to the registration message indicating whether or not the plurality of protocol-specific header suppression techniques is supported by the base station; and wherein the media access control is further configured to format data for wireless transmission to the base station in accordance with a selected one of the plurality of protocol-specific header suppression techniques if the response to the registration message indicates the plurality of protocol-specific header suppression techniques is supported by the base station.

2. The subscriber station of claim 1, wherein the media access control is further configured to format data for wireless transmission to the base station in accordance with a default header suppression technique if the response to the registration message indicates the plurality of protocol-specific header suppression techniques is not supported by the base station.

3. The subscriber station of claim 2, wherein the default header suppression technique is a standardized header suppression technique.

4. The subscriber station of claim 1, wherein the registration message is a REG-REQ message and wherein the response to the registration message is a REG-RSP message.

5. The subscriber station of claim 1, wherein the data comprises a data packet.

6. A base station in a wireless communication system, comprising:

a media access control;

a memory coupled to the media access control;

a wireless receiver coupled to the media access control; and a wireless transmitter coupled to the media access control;

wherein the wireless receiver is configured to wirelessly receive a registration message from a subscriber station and to provide the registration message to the media access control, the registration message designating support for a plurality of protocol-specific header suppression techniques or support for a default header suppression technique by the subscriber station;

wherein the media access control is configured to assign an identifier to the subscriber station and to associate the identifier with a protocol indicator in the memory, the protocol indicator indicating support for the plurality of protocol-specific header suppression techniques or support for the default header suppression technique as designated by the registration message;

wherein the wireless transmitter is configured to wirelessly transmit the identifier assigned by the media access control to the subscriber station;

wherein the wireless receiver is further configured to wirelessly receive a request for transmission opportunity from the subscriber station and to provide the request for transmission opportunity to the media access control, the request for transmission opportunity including the identifier; and wherein the media access control is further configured to allocate a transmission opportunity to the subscriber station in response to the request for transmission opportunity, to use the identifier from the request for transmission opportunity to access the protocol indicator in the memory, and to process data transmitted by the subscriber station during the allocated transmission opportunity in accordance with a selected one of the plurality of protocol-specific header suppression techniques if support for the plurality of protocol-specific header suppression techniques is indicated by the protocol indicator, and process data transmitted by the subscriber station during the allocated transmission opportunity in accordance with the default header suppression technique if support for the default header suppression technique is indicated by the protocol indicator.

7. The base station of claim 6, wherein the default header suppression technique is a standardized header suppression technique.

8. The base station of claim 6, wherein the registration message is a REG-REQ message.

9. The base station of claim 6, wherein the memory is a read-only memory or a random access memory.

10. The base station of claim 6, wherein the wireless receiver is configured to wirelessly receive the request for transmission opportunity from the subscriber station in a contention area of a first map allocation message, and wherein the media access control is configured to allocate the transmission opportunity to the subscriber station in a second map allocation message.

11. The base station of claim 6, wherein the media access control is configured to associate the identifier with the protocol indicator in the memory by storing the identifier and the protocol indicator as associated values in a look-up table in the memory, and wherein the media access control is configured to use the identifier from the request for transmission opportunity to access the protocol indicator in the memory by using the identifier to access the protocol indicator in the look-up table in the memory.

12. A subscriber station in a wireless communication system, comprising:

a media access control configured to generate a registration message that indicates support for a plurality of protocol-specific header suppression techniques;

a wireless transmitter configured to wirelessly transmit the registration message to a base station; and a wireless receiver configured:

(i) to wirelessly receive a response to the registration message from the base station, (ii) to provide the response to the registration message to the media access control, the response to the registration message indicating whether or not the plurality of protocol-specific header suppression techniques is supported by the base station, and (iii) to format data for wireless transmission to the base station in accordance with a selected one of the plurality of protocol-specific header suppression techniques if the response to the registration message indicates the plurality of protocol-specific header suppression techniques is supported by the base station.

13. The subscriber station of claim 12, wherein the media access control is further configured to format data for wireless transmission to the base station in accordance with a default header suppression technique if the response to the registration message indicates the plurality of protocol-specific header suppression techniques is not supported by the base station.

14. The subscriber station of claim 13, wherein the default header suppression technique is a standardized header suppression technique.

15. The subscriber station of claim 12, wherein the registration message is a REG-REQ message and wherein the response to the registration message is a REG-RSP message.

16. A base station in a wireless communication system, comprising:

a wireless receiver configured to wirelessly receive a registration message from a subscriber station, the registration message designating support for a plurality of protocol-specific header suppression techniques or support for a default header suppression technique by the subscriber station;

a media access control configured:

(i) to assign an identifier to the subscriber station to associate the identifier with a protocol indicator, the protocol indicator indicating support for the plurality of protocol-specific header suppression techniques or support for the default header suppression technique, (ii) to allocate a transmission opportunity to the subscriber station in response to the request for transmission opportunity, (iii) to use the identifier from the request for transmission opportunity to access the protocol indicator, (iv) to process data transmitted by the subscriber station during the allocated transmission opportunity in accordance with a selected one of the plurality of protocol-specific header suppression techniques if support for the plurality of protocol-specific header suppression techniques is indicated by the protocol indicator, and (v) to process data transmitted by the subscriber station during the allocated transmission opportunity in accordance with the default header suppression technique if support for the default header suppression technique is indicated by the protocol indicator; and a wireless transmitter configured to wirelessly transmit the identifier to the subscriber station.

17. The base station of claim 16, wherein the default header suppression technique is a standardized header suppression technique.

18. The base station of claim 16, wherein the registration message is a REG-REQ message.

19. The base station of claim 16, wherein the wireless receiver is configured to wirelessly receive the request for transmission opportunity from the subscriber station in a contention area of a first map allocation message, and wherein the media access control is configured to allocate the transmission opportunity to the subscriber station in a second map allocation message.

20. The base station of claim 16, wherein the media access control is configured to associate the identifier with the protocol indicator by storing the identifier and the protocol indicator as associated values in a look-up table in a memory, and wherein the media access control is configured to use the identifier from the request for transmission opportunity to access the protocol indicator in the memory by using the identifier to access the protocol indicator in the look-up table in the memory.

* * * * *